(12) United States Patent
O'Briain

(10) Patent No.: US 12,311,014 B1
(45) Date of Patent: May 27, 2025

(54) COMPOSITION AND USE THEREOF FOR THE TREATMENT OF EQUINE GASTRIC ULCER SYNDROME

(71) Applicant: Killian O'Briain, Westport (IE)

(72) Inventor: Killian O'Briain, Westport (IE)

( * ) Notice: Subject to any disclaimer, the term of this patent is extended or adjusted under 35 U.S.C. 154(b) by 0 days.

(21) Appl. No.: 18/889,340

(22) Filed: Sep. 18, 2024

(51) Int. Cl.
| | | |
|---|---|---|
| *A61K 31/00* | (2006.01) | |
| *A61K 31/375* | (2006.01) | |
| *A61K 33/18* | (2006.01) | |
| *A61K 33/30* | (2006.01) | |
| *A61K 38/44* | (2006.01) | |
| *A61P 1/04* | (2006.01) | |

(52) U.S. Cl.
CPC ............ *A61K 38/44* (2013.01); *A61K 31/375* (2013.01); *A61K 33/18* (2013.01); *A61K 33/30* (2013.01); *A61P 1/04* (2018.01); *C12Y 111/01007* (2013.01)

(58) Field of Classification Search
CPC ..................................................... A61K 31/00
See application file for complete search history.

(56) References Cited

U.S. PATENT DOCUMENTS

| | | | |
|---|---|---|---|
| 5,066,497 A | 11/1991 | Witkin | |
| 5,607,681 A | 3/1997 | Galley et al. | |
| 6,214,339 B1 | 4/2001 | Pellico | |
| 9,993,533 B2 | 6/2018 | Pellico | |
| 2009/0017100 A1 | 1/2009 | Shin | |
| 2022/0202797 A1 | 6/2022 | Bova et al. | |

FOREIGN PATENT DOCUMENTS

| | | |
|---|---|---|
| CA | 2365176 A1 | 10/2000 |
| EP | 2 925 335 B1 | 10/2015 |
| WO | WO-02/054872 A1 | 7/2002 |
| WO | WO-2008/045696 A2 | 4/2008 |
| WO | WO-2011/116052 A2 | 9/2011 |
| WO | WO-2012/140272 A1 | 10/2012 |
| WO | WO-2023/169664 A1 | 9/2023 |

OTHER PUBLICATIONS

Haukioja et al., "Sensitivity of Helicobacter pylori to an innate defence mechanism, the lactoperoxidase system, in buffer and in human whole saliva," J Medical Microbiology 53:855-860, 2004.*
Griffiths et al., "Discussion on the treatment of gastric ulcer," The British Medical Journal 2(2234):1041-1045, 1903.*
Adamson et al. "Lactoperoxidase and thiocyanate protect bacteria from hydrogen peroxide," Infection and Immunity. 1982, 35:1, pp. 20-24.
Eales et al., "A field study of watery mouth: clinical, epidemiological, biochemical, haematological and bacteriological observations," Vet Rec., Nov. 29, 1986, 119(22), pp. 543-547 (Abstract).
Earnshaw et al. "Inhibition of Salmonella typhimurium and E. coli in an Infant Milk Formula by an Activated Lactoperoxidase System," J Food Prot., Feb. 1990, 53(2), pp. 170-172.
Erttmann et al. "Hydrogen peroxide release by bacteria suppresses inflammasome-dependent innate immunity," Nature Communications, 2019, 10:3493, pp. 1-13.
Fonty et al. "Establishment of the microflora and anaerobic fungi in the rumen of lambs" Journal of General Microbiology, 1987, 133, pp. 1835-1843.
Garcia-Graells et al., "Inactivation of *Escherichia coli* and *Listeria innocua* in milk by combined treatment with high hydrostatic pressure and the lactoperoxidase system," Appl Environ Microbiol., 2000, 66(10), pp. 4173-4179.
Min et al. "Inhibition of Penicillium commune by Edible Whey Protein Films Incorporating Lactoferrin, Lacto-ferrin Hydrolysate, and Lactoperoxidase Systems," Journal of Food Science, Mar. 1, 2005, vol. 70, No. 2, pp. M87-M94.
Ramp et al. "Hydrogen Peroxide Inhibits Glucose Metabolism and Collagen Synthesis in Bone," J. Periodontal, May 1987, vol. 58 No. 5, pp. 340-344.
Rubin et al. "Mechanisms of the Killing of Cultured Hepatocytes by Hydrogen Peroxide," Archives of Biochemistry and Biophysics, Feb. 1, 1984, vol. 228, pp. 450-459.
Swords et al. "Postnatal changes in selected bacterial groups of the pig colonic microflora," Biol. Neon. 1993, 63, pp. 191-200.
Tonoyan et al. "Antimicrobials offered from nature: Peroxidase-catalyzed systems and their mimics," Biochemical Pharmacology, Oct. 17, 2020, vol. 182, pp. 1-15.
Vokes et al. "Equine Gastric Ulcer Syndrome: An Update on Current Knowledge Animals," 2023, vol. 13, No. 1261, pp. 1-25.

* cited by examiner

*Primary Examiner* — Rosanne Kosson
(74) *Attorney, Agent, or Firm* — Foley & Lardner LLP

(57) ABSTRACT

Compositions comprising lactoperoxidase and one or more iodide salts for treating equine gastric ulcer syndrome.

26 Claims, No Drawings

COMPOSITION AND USE THEREOF FOR THE TREATMENT OF EQUINE GASTRIC ULCER SYNDROME

CROSS-REFERENCE TO RELATED APPLICATIONS

This application claims priority under 35 U.S.C. § 119(a) of European Patent Application No. 23211903.2, filed on Nov. 24, 2023 and UK Patent Application No. GB2317960.9, filed on Nov. 24, 2023. The entire contents of each of which are incorporated by reference herein.

FIELD

The present invention is concerned with a pharmaceutical composition for use in treating or preventing equine gastric ulcer syndrome. In particular, the present invention is concerned with a pharmaceutical composition for use in treating equine squamous gastric disease and/or equine glandular gastric disease. Also provided is a feed additive or dietary supplement composition which is useful for treating, including prophylactically treating, equine gastric ulcer syndrome, such as equine squamous gastric disease and/or equine glandular gastric disease.

The present invention is also concerned with pharmaceutical compositions for use in treating gastrointestinal bacterial infections in a mammal. The composition is particularly effective for treating bacterial infections in mammals, such as lambs, calves, humans, pigs and horses. Suitably, the mammals may be monogastric mammals. Also provided is a feed additive or dietary supplement composition which is useful for treating, including prophylactically treating, gastrointestinal bacterial infections in animals.

The invention further provides animal feed comprising the feed additive or dietary supplement composition disclosed herein. The compositions disclosed are useful for ameliorating gastrointestinal bacterial infections without requiring antibiotics.

In addition, the compositions of the present invention are useful for treating stomach ulcers, particularly in horses, cats and dogs.

BACKGROUND

Equine gastric ulcer syndrome (EGUS) describes the development of ulcers on the inner wall of the stomach of a horse. Ulcers can vary in severity from a minor inflammation of the stomach lining through to severe ulceration and bleeding, with perforation of the stomach potentially leading to colic and sudden death.

The stomach of the horse is comprised of two distinct regions, the squamous and glandular mucosa, separated by the margo plicatus. The glandular mucosa lines the ventral portion of the stomach and consists of gastric glands that secrete hydrochloric acid, pepsinogen, histamine, mucous, and sodium bicarbonate. The dorsal portion of the stomach is covered by squamous epithelium. The glandular mucosa lines approximately the lower two thirds of the stomach, whereas the squamous mucosa lines the upper third of the stomach. Ulceration of the stomach has been divided based upon ulcer/lesion location: equine glandular gastric disease (EGGD) refers to disease of the glandular portion of the stomach, and equine squamous gastric disease (ESGD) refers to disease of the squamous portion of the stomach. Equine gastric ulcer syndrome (EGUS) refers to disease of any portion of the stomach and is the umbrella term used.

Gastric ulcers are sores which form on the lining of the stomach. These are extremely prevalent in horses with an estimated 50-90% of horses suffering from ulceration. EGUS can be a major cause of poor athletic performance in racehorses, where prevalence of ulcers is very high. Ulcers occur from a variety of sources: racehorses are typically fed grain-rich diets, with lengthy fasting periods between meals when exercise is carried out; exercise has been shown to increase gastric acid production and decreases blood flow to the GI tract, this coupled with reduced saliva production and indoor confinement are thought to lead to the contribution of stomach ulcers. Increased levels of gastric ulcers are associated with an increased risk of colic.

As outlined above. EGUS is highly prevalent particularly in high performance horses, and increases significantly in horses that are in training. EGUS is considered to result from disequilibrium between mucosal aggressive factors such as hydrochloric acid, pepsin, bile acids and organic acids, and mucosal protective factors such as mucus and bicarbonate.

Current therapeutic strategies follow the mantra "no acid, no ulcer" and focus on neutralising existing gastric acid or blocking new gastric acid secretion to increase stomach pH. Suppression of gastric acid production can be achieved by using proton pump inhibitors such as rabeprazole, lansoprazole, dexlansoprazole, tenatoprazole, omeprazole and esomeprazole.

EGUS can be treated by protecting the damaged gastric mucosa with mucosal protectants such as sucralfate (which is given orally) and misoprostol (which is given by injection), by neutralising gastric acid with antacids such as magnesium hydroxide, or by suppressing acid production by the oral use of proton pump inhibitors (PPI) or histamine type 2 (H2) receptor antagonists such as ranitidine.

There are several drawbacks with such treatments. Mucosal protectants must be continuously present and available at all sites of ulceration to allow ulcers to heal. This requires high doses of the mucosal protectant and frequent administration, at last twice daily for both sucralfate and misoprostol. Similarly, antacids must be present constantly in the stomach and in sufficient quantity to neutralise the significant quantity of continuously produced gastric HCl. The most effective approaches are those which suppress acid production. Currently there is one approved pharmaceutical treatment for stomach ulcers in horses, Omeprazole, which causes a reduction in gastric acid production.

US20220202797A1 describes a method of treating and/or preventing gastric ulcers, said method comprising administering by injection a therapeutically effective amount of a composition comprising: a) a first agent selected from the group consisting of: a medium chain triglyceride and a long chain triglyceride; and b) a second agent comprising a proton pump inhibitor or pharmaceutically or veterinary acceptable salt, wherein the composition is adapted for sustained release of a therapeutically effective amount of the proton pump inhibitor to a subject in need thereof. The proton pump inhibitor is omeprazole.

EP2925335B1 is concerned with a composition for use in a method of preventing rebound ulcers in horses after administration of omeprazole or in a method of treating Equine Gastric Ulcer Syndrome in a horse in need thereof, comprising administering to the horse a therapeutically effective amount of the composition, wherein the composition comprises: (i) a preparation obtained from sea buckthorn, wherein the preparation obtained from sea buckthorn is a concentrate, metabolite, constituent, or extract, or a combination thereof of the sea buckthorn fruits, (ii) glutamine and (iii) aloe vera extract, pectin, and lecithin.

*Helicobacter* species have been implicated in gastric and duodenal ulceration in humans, however, reports indicate that *helicobacter* is not associated with EGUS in horses.

The area of nutraceuticals is continually evolving and the use of omega-3 rich sources of oil have become increasingly popular. A recent study evaluating the supplementation of exercising Thoroughbreds showed long chain polyunsaturated fatty acids derived from fish to be superior at protecting against ESGD and altering inflammatory profiles, when compared to combined polyunsaturated fatty acids derived from a corn and flax blend.

The use of omeprazole in humans is associated with complications, including rebound gastric hyperacidity, increase in antimicrobial and non-specific diarrhea risk and increased fracture risk. Concerns have also been raised about the potential for omeprazole to increase fracture risk in horses. Long term omeprazole therapy to prevent EGUS is therefore not recommended. It would be advantageous to have an efficient, low cost alternative treatment, and preventative solution that could be readily administered for example by oral administration to horses to manage, treat, and or prevent EGUS. The present invention provides such a solution.

Lactoperoxidase is a peroxidase enzyme secreted from mammary, salivary and other mucosal glands. Lactoperoxidase catalyses the oxidation of several inorganic and organic substrates by hydrogen peroxide, for example, lactoperoxidase catalyses hydrogen peroxide oxidation of thiocyanate to hypothiocyanate, bromide to hypobromite and iodide to hypoiodite. The oxidised species are generally short lived but they can have potent bactericidal effects.

The lactoperoxidase system involves the use of lactoperoxidase, thiocyanate and hydrogen peroxide as a chemical preservative for raw milk where refrigeration is not available. The lactoperoxidase catalyses the oxidation of thiocyanate ions in the presence of hydrogen peroxide into hypohthiocyanous acid. The acid dissociates in milk and hypothiocyanite ions, are thought to be responsible for the antimicrobial effect of the lactoperoxidase system.

The precise mechanism underpinning the antimicrobial nature of the LPO system is unknown. A multitude of experimental protocols, with reports of bacterial inhibition have been described, but often bacterial regrowth occurs after a period of time, and as such the effect observed is bacteriostatic rather than bactericidal effect.

International patent application publication number WO2012/140272 is concerned with a microbiocidal composition comprising a reactive oxygen species or components capable of producing a reactive species, the composition being capable of delivering the reactive oxygen species to a level of at least 0.4 millimoles per litre over a 24-hour period. Example compositions comprise potassium iodide, lactoperoxidase and glucose oxidase. Glucose oxidase is an oxidoreductase that catalyses the oxidation of glucose to produce hydrogen peroxide and D-glucono-β-lactone. The composition may be used to treat bacterial infections, or for control of bacterial contamination, which avoids the use of antibiotics. Such infections include mastitis, tuberculosis, cystic fibrosis and other lung infections, and the contamination that may result from biofilm formation on surfaces such as on medical devices. However, the composition is also suitable for the treatment of viral, yeast or fungal infections or for the control of contamination by such organisms.

U.S. Pat. No. 5,066,497 discloses an antimicrobial solution comprising from 0.01% to 2% of iodine derived from povidone-iodine complex and about 0.5% to 5% of hydrogen peroxide as a nascent oxygen source. The solution is described as having utility in treating mastitis.

Current commercial applications based on the lactoperoxidase system include mouth wash, toothpaste, food preservation and disinfectants, which are mainly based on inhibition of microbial growth, rather than the killing of cells and the total elimination of bacterial populations from various settings.

U.S. Pat. No. 5,607,681 discloses a composition comprising iodide anions, thiocyanate anions, D-glucose, glucose oxidase and lactoperoxidase. The compositions are described as having utility as preservatives which prevent microbial spoilage of a wide range of products such as, for example, cosmetic, toiletry and pharmaceutical formulations, domestic household and industrial preparations such as, for example, detergents, and foodstuffs such as, for example, milk and milk products and animal feedstuffs. This patent describes activity against bacteria for up to 72 hours and fails to describe a therapeutic application of the system.

Watery mouth disease is a term to describe a collection of clinical signs in newborn lambs. These signs include profuse salivation, bloating, retained meconium, lethargy and failure to suck. This is caused by *E. coli* infection and colonisation of the small intestine, with rapid growth of the bacteria and release of toxins. The disease is considered to be caused by poor hygiene e.g. ingestion of *E. coli* from the ewe's fleece as they seek the udder, or through soiled bedding, leading to bacterial infection and delayed or inadequate intake of colostrum in the first hours of life. This is particularly an issue in intensive indoor settings, with watery mouth causing severe losses, with morbidity sometimes reaching 24% and mortality of those affected as high as 83% (Eales F A, Small J, Gilmour J S, Donachie W, FitzSimons J, Dingwall W S. A field study of watery mouth: clinical, epidemiological, biochemical, haematological and bacteriological observations. Vet Rec. 1986 Nov. 29; 119(22): 543-7). Watery mouth disease is generally treated by administering antibiotics to the affected lambs. For example, lambs may be treated with neomycin, streptomycin and/or amoxicillin. Furthermore, lambs are often treated prophylactically with antibiotics to avoid development of bacterial infections such as *E. coli* infection.

Colibacillosis, or *E. coli* infection, is a major disease of pigs, typically causing illness and death in neonatal and recently weaned pigs. This is becoming a major disease of clinical and economic importance in the pig industry. The most common method for the treatment of colibacillosis is through use of antibiotics, both as a prophylactic and as a metaphylactic. Due to concerns over the rise of antimicrobial resistance and transfer through the food chain, alternative solutions are required. Furthermore, in the pig industry, a common approach for controlling *E. coli* infection in newly weaned piglets is to include zinc oxide in their diet; zinc oxide may be included at a rate of 3 wt % of feed. Large quantities of zinc oxide (e.g. over 1 wt % based on the quantity of feed) will be prohibited as a feed additive in porcine diets in the EU once products which were placed on the marked in advance of July 2022 are exhausted, thus an alternative approach to address bacterial infection in piglets is required.

WO02/054872 describes a liquid antimicrobial composition comprising (i) a mixture of iodide anions and thiocyanate anions, (ii) periodic acid or an alkali metal salt thereof, and optionally, a peroxidase. The composition may be used as a microbiocide.

WO2008045696A2 describes a therapeutic composition for treatment of vaginal diseases that employs peroxide producing enzymes and peroxidases. The composition may comprise inter alia lactoperoxidase and glucose oxidase.

Herein, compositions, treatments, feed additives and dietary supplements are described. The compositions have utility in treating, preventing, ameliorating or reducing the impact of EGUS, including EGGD and/or EGSD. Furthermore, compositions of the invention have utility in treating, preventing and/or ameliorating watery mouth disease in lambs, and colibacillosis as well as diarrhea and scour in pigs, and/or bovine calves, particularly bovine dairy calves. The compositions have utility in reducing the impact of bacterial infections in mammals, in particular, in animals such as lambs, bovines particularly calves, such as dairy calves, pigs, horses and humans.

SUMMARY

In one aspect, the present invention provides a composition, such as a pharmaceutical composition, comprising: lactoperoxidase, an iodide salt, and a pharmaceutically acceptable carrier and/or excipient, for use in the treatment or prevention of equine gastric ulcer syndrome (EGUS), optionally wherein the equine gastric ulcer syndrome comprises equine squamous gastric disease (ESGD) and/or equine glandular gastric disease (EGGD).

The composition is for treating EGUS, such as ESGD and/or EGGD in equids, such as in horses and/or ponies. The horses may be high performance horses, such as racehorses, showjumpers, hunters, eventers, or a pleasure horse or pony.

The composition may not comprise a peroxide, or a source of peroxide. Suitably, the treatment does not comprise administration of a peroxide or a source of peroxide.

The composition may not comprise thiocyanate, or a source of thiocyanate. Suitably, the treatment does not comprise administration of a thiocyanate or a source of thiocyanate.

Suitably, the lactoperoxidase and iodide salt are in a weight ratio of from 1:10 to 10:1, preferably, from 1:3 to 3:1, most preferably from 1:1.3 to 1.3:1, such as about 1:1.

The iodide salt may be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The composition is suitably an oral dosage form, for example a solid dosage form, such as a tablet form or powder form, or a liquid dosage form, including a suspension. The composition is formulated for oral administration.

The composition may further comprise vitamin C.

The composition may comprise two or more excipients.

The composition may comprise one or more of magnesium stearate, lactose, dextrose, microcrystalline cellulose, starch (corn), silica (silicon dioxide), titanium dioxide, zinc oxide, colostrum, hydroxypropyl methyl cellulose, stearic acid, sodium starch glycolate, gelatin, talc, sucrose, calcium stearate, and povidone. For example, the composition may comprise magnesium stearate, microcrystalline cellulose, zinc oxide and colostrum.

Suitably, the treatment or prevention of equine gastric ulcer syndrome such as equine squamous gastric disease and/or equine glandular gastric disease comprises administration of at least 0.24 mmol of the iodide salt, and at least 40 mg of the lactoperoxidase on a daily basis, preferably, the treatment comprises administration of at least 0.36 mmol of the iodide salt and at least 60 mg of the lactoperoxidase on a daily basis, more preferably, the treatment comprises administration of at least 0.48 mmol of the iodide salt and at least 80 mg of the lactoperoxidase on a daily basis.

For example, the treatment may comprise administration of 40 mg of the iodide salt, and at least 40 mg of the lactoperoxidase on a daily basis, preferably, the treatment comprises administration of at least 60 mg of the iodide salt and at least 60 mg of the lactoperoxidase on a daily basis, more preferably the treatment comprises administration of at least 80 mg of the iodide salt and at least 80 mg of the lactoperoxidase on a daily basis.

Suitably, the treatment comprises administration of 0.24 mmol to 1.2 mmol of the iodide salt on a daily basis, such as from 0.36 mmol to 1.2 mmol, for example 0.48 mmol to 1.2 mmol of the iodide salt on a daily basis. Suitably, the treatment comprises administration of from 0.24 mmol to 0.6 mmol of the iodide salt on a daily basis, such as 0.36 mmol to 0.6 mmol, for example 0.48 mmol to 0.6 mmol of the iodide salt on a daily basis. For example, the treatment may comprise administration of 0.24 mmol to 0.51 mmol of the iodide salt on a daily basis, such as 0.36 mmol to 0.51 mmol, or 0.48 mmol to 0.51 mmol of the iodide salt on a daily basis.

For example, the treatment may comprise administration of 40 to 200 mg of the iodide salt on a daily basis, such as from 60 to 200 mg of the iodide salt on a daily basis, for example from 80 to 200 mg of the iodide salt on a daily basis. The treatment may comprise administration of 40 to 100 mg of the iodide salt on a daily basis, such as 60 to 100 mg of the iodide salt on a daily basis, for example from 80 to 100 mg of the iodide salt on a daily basis. For example, the treatment may comprise administration of 40 to 85 mg of the iodide salt on a daily basis on a daily basis. For example, when the treatment comprises administration of a composition comprising potassium iodide, the treatment may comprise administration of 40 to 200 mg of the potassium iodide on a daily basis, preferably, 40 to 100 mg of the potassium iodide salt on a daily basis, such as 60 to 100 mg of the potassium iodide salt on a daily basis optionally from 80 to 100 mg of the potassium iodide salt on a daily basis. Most preferably the treatment comprises administration of 40 to 85 mg of the potassium salt on a daily basis.

The treatment may comprise administration of 40 to 200 mg of the lactoperoxidase on a daily basis, such as 60 to 200 mg of the lactoperoxidase on a daily basis, for example 80 to 200 mg of the lactoperoxidase on a daily basis. Optionally, the treatment may comprise administration of 40 to 100 mg of the lactoperoxidase on a daily basis, such as 60 to 100 mg of the lactoperoxidase on a daily basis, for example 80 to 100 mg of the lactoperoxidase on a daily basis. Most preferably the treatment may comprise administration of 40 to 85 mg of the lactoperoxidase on a daily basis.

The treatment may comprise administration of 0.24 mmol to 1.2 mmol of the iodide salt and 40 to 200 mg of the lactoperoxidase on a daily basis, such as 0.24 mmol to 0.6 mmol of the iodide salt and 40 to 100 mg of the lactoperoxidase on a daily basis, for example from 0.36 mmol to 0.6 mmol of the iodide salt and from 60 mg to 100 mg of the lactoperoxidase on a daily basis, optionally from 0.48 mmol to 0.6 mmol of the iodide salt and from 80 mg to 100 mg of the lactoperoxidase on a daily basis. Further optionally, treatment may comprise administration of from 0.24 mmol to 0.51 mmol of the iodide salt and 40 to 85 mg of the lactoerpoxidase on a daily basis.

Suitably, the treatment may comprise administration of 40 to 200 mg of the iodide salt and 40 to 200 mg of the lactoperoxidase on a daily basis, for example 60 mg to 200 mg of the iodide salt and from 60 mg to 200 mg of the lactoperoxidase on a daily basis, optionally from 80 mg to 200 mg of the iodide salt and from 80 mg to 200 mg of the lactoperoxidase on a daily basis. Suitably, the treatment may comprise administration of from 40 mg to 100 mg of the iodide salt and 40 to 100 mg of the lactoperoxidase on a daily basis, such as from 60 mg to 100 mg of the iodide salt and 60 to 100 mg of the lactoperoxidase on a daily basis, for example from 80 mg to 100 mg of the iodide salt and 80 to 100 mg of the lactoperoxidase on a daily basis. More suitably, the treatment may comprise administration of 40 mg to 85 mg of the iodide salt and 40 to 85 mg of the lactoperoxidase on a daily basis.

Suitably, the treatment is continued for a period of at least four weeks, preferably at least 8 weeks, more preferably at least 12 weeks. Most preferably the treatment comprises administration of the composition on a daily basis, for example administration daily while the equid, e.g. horse, is in training. The treatment may comprise administration of the composition on a daily basis at least four days per week, preferably, at least 5 days per week.

The composition, such as a pharmaceutical composition, for use in treating and/or preventing EGUS, such as EGSD and/or EGGD described herein may be formulated as one or more unit doses.

The unit dose of the composition may comprise lactoperoxidase present in an amount of from 0.5 mg to 200 mg, such as from 1 mg to 100 mg, preferably from 5 mg to 50 mg, more preferably from 8 mg to 20 mg, such as from 8 mg to 12 mg.

The unit dose of the composition may comprise iodide salt present in an amount of from 0.003 mmol to 1.2 mmol, such as from 0.006 mmol to 0.6 mmol, preferably from 0.030 mmol to 0.30 mmol, more preferably from 0.048 mmol to 0.072 mmol.

For example, a unit dose of the composition may comprise iodide salt present in an amount of from 0.5 mg to 200 mg, such as from 1 mg to 100 mg, preferably from 5 mg to 50 mg, more preferably from 8 mg to 20 mg, such as from 8 mg to 12 mg.

The unit dose of the composition may comprise lactoperoxidase present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the unit dose.

The unit does of the composition comprises iodide salt, is present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the unit dose.

Suitably, the unit dose of the composition comprises lactoperoxidase present in an amount of from about 8 mg to about 20 mg, and in an amount of from about 0.5 wt % to about 5 wt % based on the total weight of the unit dose, and wherein the iodide salt is potassium iodide, and is present in an amount of from about 8 mg to about 20 mg, and in an amount of from about 0.5 wt % to about 5 wt % based on the total weight of the unit dose, and wherein said composition comprises optionally comprises vitamin C, and optionally comprises zinc oxide. Optionally, at least 5 unit doses are administered daily, optionally, at least 6 unit doses are administered daily, optionally, at least 8 unit doses are administered daily, preferably, at least 10 unit doses are administered daily.

The number of unit doses administered is adjusted in order to deliver the desired dose. E.g. where a unit dose comprises 8 mg lactoperoxidase and 8 mg KI, in order to achieve a daily dose of 80 mg lactoperoxidase and 80 mg KI, 10 unit doses are administered.

Suitably, the unit dose of the composition comprises lactoperoxidase present in an amount of from about 8 mg to about 20 mg, and in an amount of from about 0.5 wt % to about 5 wt % based on the total weight of the unit dose, and wherein the iodide salt is potassium iodide, and is present in an amount of from about 8 mg to about 20 mg, and in an amount of from about 0.5 wt % to about 5 wt % based on the total weight of the unit dose, and wherein said composition comprises optionally comprises vitamin C, and optionally comprises zinc oxide, and at least 6 unit doses are administered on a daily basis, optionally at least 8 unit doses are administered on a daily basis, preferably at least 10 unit doses are administered on a daily basis.

For example, the unit dose of the composition may comprise lactoperoxidase present in an amount of from about 8 mg to about 12 mg, and in an amount of from about 0.5 wt % to about 5 wt % based on the total weight of the unit dose, the iodide salt is potassium iodide, and is present in an amount of from about 8 mg to about 12 mg, and in an amount of from about 0.5 wt % to about 5 wt % based on the total weight of the unit dose, and wherein said composition comprises optionally comprises vitamin C, and optionally comprises zinc oxide, and at least 6 unit doses are administered on a daily basis, optionally at least 8 unit doses are administered on a daily basis, preferably at least 10 unit doses are administered on a daily basis.

The composition, such as a pharmaceutical composition, for use described herein may be formulated as a feed additive or dietary supplement as described herein.

In another aspect, the present invention provides a combination for use in the treatment of equine gastric ulcer syndrome such as equine squamous gastric disease and/or equine glandular gastric disease, the combination comprising: a lactoperoxidase; and an iodide salt; wherein the lactoperoxidase and iodide salt are administered sequentially or simultaneously to an equid, such as a horse or pony.

Suitably the lactoperoxidase and the iodide salt are in a relative weight ratio of from 1:10 to 10:1, preferably, in a relative weight ratio of from about 1:2 to 2:1, more preferably in a relative weight ratio of from about 1:1.3 to 1.3:1.

The combination is for treating EGUS, such as ESGD and/or EGGD in equids, such as in horses and/or ponies. The horses may be high performance horses, such as racehorses, showjumpers, hunters, eventers, or pleasure horses or ponies.

Suitably, the combination does not comprise a peroxide or a source of peroxide. Suitably, the treatment does not comprise administration of a peroxide or a source of peroxide.

Suitably, the combination does not comprise a thiocyanate or a source of thiocyanate. Suitably, the treatment does not comprise administration of a thiocyanate or a source of thiocyanate.

The iodide salt may be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The combination may involve administration of one or more oral dosage forms. The oral dosage form may be a solid dosage form, such as a tablet or powder, or a liquid dosage form, including a suspension.

The combination may further comprise vitamin C.

The combination may comprise one or more excipients. For example, the one or more oral dosage forms may comprise one or more excipients.

The combination for example the one or more oral dosage forms may comprise one or more of magnesium stearate, lactose, dextrose, microcrystalline cellulose, starch (corn), silica (silicon dioxide), titanium dioxide, zinc oxide, colostrum, hydroxypropyl methyl cellulose, stearic acid, sodium starch glycolate, gelatin, talc, sucrose, calcium stearate, and povidone. For example, the composition may comprise magnesium stearate, microcrystalline cellulose, zinc oxide and colostrum.

The combination for example the one or more oral dosage forms may comprise one or more flavourings, sweeteners, and/or pigments.

As outlined above, the treatment of equine gastric ulcer syndrome such as equine squamous gastric disease and/or equine glandular gastric disease suitably comprises administration of at least 0.24 mmol of the iodide salt, and at least 40 mg of the lactoperoxidase on a daily basis, preferably, the treatment comprises administration of at least 0.36 mmol of the iodide salt and at least 60 mg of the lactoperoxidase on a daily basis, more preferably, the treatment comprises administration of at least 0.48 mmol of the iodide salt and at least 80 mg of the lactoperoxidase on a daily basis. For example, the treatment may comprise administration of 40 mg of the iodide salt, and at least 40 mg of the lactoperoxidase on a daily basis, preferably, the treatment comprises administration of at least 60 mg of the iodide salt and at least 60 mg of the lactoperoxidase on a daily basis, more preferably the treatment comprises administration of at least 80 mg of the iodide salt and at least 80 mg of the lactoperoxidase on a daily basis.

Suitably, the treatment comprises administration of 0.24 mmol to 1.2 mmol of the iodide salt on a daily basis, such as from 0.36 mmol to 1.2 mmol, for example from 0.48 mmol to 1.2 mmol of the iodide salt on a daily basis. Suitably, the treatment comprises administration of from 0.24 mmol to 0.6 mmol of the iodide salt on a daily basis, such as 0.36 mmol to 0.6 mmol, for example 0.48 mmol to 0.6 mmol of the iodide salt on a daily basis. For example, the treatment may comprise administration of 0.24 mmol to 0.51 mmol of the iodide salt on a daily basis, such as 0.36 mmol to 0.51 mmol, or 0.48 mmol to 0.51 mmol of the iodide salt on a daily basis.

For example, the treatment may comprise administration of 40 to 200 mg of the iodide salt on a daily basis, such as from 60 to 200 mg of the iodide salt on a daily basis, for example from 80 to 200 mg of the iodide salt on a daily basis. The treatment may comprise administration of 40 to 100 mg of the iodide salt on a daily basis, such as 60 to 100 mg of the iodide salt on a daily basis, for example from 80 to 100 mg of the iodide salt on a daily basis. For example, the treatment may comprise administration of 40 to 85 mg of the iodide salt on a daily basis on a daily basis. For example, when the treatment comprises administration of a composition comprising potassium iodide, the treatment may comprise administration of 40 to 200 mg of the potassium iodide on a daily basis, preferably, 40 to 100 mg of the potassium iodide salt on a daily basis, such as 60 to 100 mg of the potassium iodide salt on a daily basis optionally from 80 to 100 mg of the potassium iodide salt on a daily basis. Most preferably the treatment comprises administration of 40 to 85 mg of the potassium salt on a daily basis.

The treatment may comprise administration of 40 to 200 mg of the lactoperoxidase on a daily basis, such as 60 to 200 mg of the lactoperoxidase on a daily basis, for example 80 to 200 mg of the lactoperoxidase on a daily basis. Optionally, the treatment may comprise administration of 40 to 100 mg of the lactoperoxidase on a daily basis, such as 60 to 100 mg of the lactoperoxidase on a daily basis, for example 80 to 100 mg of the lactoperoxidase on a daily basis. Most preferably the treatment may comprise administration of 40 to 85 mg of the lactoperoxidase on a daily basis.

The treatment may comprise administration of 0.24 mmol to 1.2 mmol of the iodide salt and 40 to 200 mg of the lactoperoxidase on a daily basis, such as 0.24 mmol to 0.6 mmol of the iodide salt and 40 to 100 mg of the lactoperoxidase on a daily basis, for example from 0.36 mmol to 0.6 mmol of the iodide salt and from 60 mg to 100 mg of the lactoperoxidase on a daily basis, optionally from 0.48 mmol to 0.6 mmol of the iodide salt and from 80 mg to 100 mg of the lactoperoxidase on a daily basis. Further optionally, treatment may comprise administration of from 0.24 mmol to 0.51 mmol of the iodide salt and 40 to 85 mg of the lactoperoxidase on a daily basis.

Suitably, the treatment may comprise administration of 40 to 200 mg of the iodide salt and 40 to 200 mg of the lactoperoxidase on a daily basis, for example 60 mg to 200 mg of the iodide salt and from 60 mg to 200 mg of the lactoperoxidase on a daily basis, optionally from 80 mg to 200 mg of the iodide salt and from 80 mg to 200 mg of the lactoperoxidase on a daily basis. Suitably, the treatment may comprise administration of from 40 mg to 100 mg of the iodide salt and 40 to 100 mg of the lactoperoxidase on a daily basis, such as from 60 mg to 100 mg of the iodide salt and 60 to 100 mg of the lactoperoxidase on a daily basis, for example from 80 mg to 100 mg of the iodide salt and 80 to 100 mg of the lactoperoxidase on a daily basis. More suitably, the treatment may comprise administration of preferably, 40 mg to 85 mg of the iodide salt and 40 to 85 mg of the lactoperoxidase on a daily basis.

Suitably, the treatment is continued for a period of at least four weeks, preferably at least 8 weeks, more preferably at least 12 weeks. Most preferably the treatment is administered daily, for example daily while the equid, e.g. horse, is in training.

The combination may comprise at least 0.24 mmol of the iodide salt, and at least 40 mg of lactoperoxidase. Preferably, the combination may comprise at least 0.36 mmol of the iodide salt and at least 60 mg of the lactoperoxidase, more preferably the combination comprises at least 0.48 mmol of the iodide salt and at least 80 mg of the lactoperoxidase.

Suitably, the combination comprises 0.24 mmol to 1.2 mmol iodide salt, preferably, 0.24 to 0.60 mmol iodide salt, more preferably, 0.24 mmol to 0.51 mmol iodide salt.

For example, the combination may comprise 40 to 200 mg iodide salt, preferably, 40 to 100 mg iodide salt, more preferably, 40 to 85 mg iodide salt. Suitably, the combination may comprise 40 to 200 mg potassium iodide, preferably, 40 to 100 mg potassium iodide, more preferably, 40 to 85 mg potassium iodide.

Suitably, the combination comprises 40 to 200 mg lactoperoxidase, preferably, 40 to 100 mg lactoperoxidase, more preferably, 40 to 85 mg lactoperoxidase.

For example, the combination may comprise at least 40 mg of the iodide salt, and at least 40 mg of lactoperoxidase. Preferably, the combination may comprise at least 60 mg of the iodide salt and at least 60 mg of the lactoperoxidase. More preferably, the combination comprises at least 80 mg of the iodide and at least 80 mg of the lactoperoxidase.

Preferably, the combination is administered on a daily basis. The combination may be formulated as a feed additive, as described herein.

Also disclosed is a method for treating and/or preventing EGUS, optionally, wherein said EGUS is EGSD or EGGD, said method comprising administering to an equid in need thereof, a composition or combination as disclosed herein, preferably, on a daily basis, or for a period as disclosed herein.

Also disclosed is a feed additive composition or dietary/feed supplement composition comprising: lactoperoxidase, and an iodide salt, wherein the composition does not comprise a peroxide or a source of peroxide; and wherein the composition does not comprise thiocyanate, or a source of thiocyanate; wherein the lactoperoxidase is present in an amount of at least 40 mg, and wherein the iodide salt is present in an amount of at least 0.24 mmol.

Optionally, the weight ratio of the lactoperoxidase to the iodide salt is in the range of from 1:2 to 2:1, such as from 1:1.3 to 1.3:1.

The iodide salt may be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The composition may be in tablet form, powder form, or oral suspension form.

The feed additive composition or dietary supplement composition may comprise at least 0.24 mmol of the iodide salt, and at least 40 mg of the lactoperoxidase, preferably, at least 0.36 mmol of the iodide salt and at least 60 mg of the lactoperoxidase, more preferably, at least 0.48 mmol of the iodide salt and at least 80 mg of the lactoperoxidase.

The feed additive composition or dietary supplement composition may comprise 0.24 mmol to 1.2 mmol of the iodide salt, preferably, 0.24 mmol to 0.6 mmol of the iodide salt, ptionally, the feed additive comprises 0.36 mmol to 1.2 mmol of the iodide salt, such as 0.36 mmol to 0.6 mmol of the iodide salt, most preferably 0.24 mmol to 0.51 mmol of the iodide salt.

For example, the feed additive composition or dietary supplement composition may comprise 40 to 200 mg of the iodide salt, preferably, 40 to 120 mg of the iodide salt, such as 40 mg to 100 mg of the iodide salt, most preferably 40 to 85 mg of the iodide salt. For example, when the iodide salt comprises potassium iodide, the feed additive composition or dietary supplement composition may comprise 40 to 200 mg of the potassium iodide, preferably, 40 to 120 mg of the potassium iodide, such as 40 to 100 mg of the potassium iodide, most preferably 40 to 85 mg.

The feed additive composition or dietary supplement composition may comprise 40 to 200 mg of the lactoperoxidase, preferably, 40 to 120 mg of the lactoperoxidase, such as 40 to 100 mg of the lactoperoxidase, most preferably 40 to 85 mg of the lactoperoxidase.

The feed additive composition or dietary supplement composition may be formulated as a unit dosage form. The feed additive composition or dietary supplement composition may be administered as one or more unit doses. Preferably the feed additive composition or dietary supplement composition is administered to equids (e.g. horses or ponies) on a daily basis.

Suitably, a unit dose of the feed additive composition or feed supplement composition may comprise 5 to 20 mg lactoperoxidase, preferably, 8 to 15 mg lactoperoxidase, more preferably, 8 to 12 mg lactoperoxidase.

The unit dose of the feed additive composition or feed supplement composition may comprise lactoperoxidase present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the unit dose.

Suitably, a unit dose of the feed additive composition or feed supplement composition may comprise 5 to 20 mg lactoperoxidase, preferably, 8 to 15 mg lactoperoxidase, more preferably 8 to 12 mg lactoperoxidase, and wherein the lactoperoxidase is present in an amount of from about 0.5 wt % to about 5 wt % based on the total weight of the unit dose, preferably in an amount of from 1 wt % to about 2 wt % based on the total weight of the unit dose.

A unit dose of the feed additive composition or feed supplement composition may comprise 0.03 mmol to 0.12 mmol iodide salt, preferably, 0.048 mmol to 0.09 mmol iodide salt, more preferably, 0.048 mmol to 0.072 mmol iodide salt.

The unit dose of the feed additive composition or feed supplement composition may comprise iodide salt present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the unit dose.

Suitably, a unit dose of the feed additive composition or feed supplement composition comprises 0.03 mmol to 0.12 mmol iodide salt, preferably, 0.048 mmol to 0.09 mmol iodide salt, more preferably, 0.048 mmol to 0.072 mmol iodide salt, and wherein the iodide salt is present in an amount of from about 0.5 wt % to about 5 wt % based on the total weight of the unit dose, preferably in an amount of from 1 wt % to about 2 wt % based on the total weight of the unit dose.

For example, a unit dose of the feed additive composition or feed supplement composition may comprise 5 to 20 mg lactoperoxidase and 0.03 mmol to 0.12 mmol iodide salt, wherein the lactoperoxidase is present in an amount of from about 0.5 wt % to about 5 wt % based on the total weight of the unit dose and wherein the iodide salt is present in an amount of from about 0.5 wt % to about 5 wt % based on the total weight of the unit dose.

In a particularly preferred aspect a unit dose of the feed additive composition or feed supplement composition comprises 8 to 15 mg lactoperoxidase and 0.048 mmol to 0.09 mmol iodide salt, wherein the lactoperoxidase is present in an amount of from about 0.5 wt % to about 5 wt %, (even further preferably from about 1 wt % to about 2 wt %) based on the total weight of the unit dose and wherein the iodide salt is present in an amount of from about 0.5 wt % to about 5 wt % (even further preferably from about 1 wt % to about 2 wt %) based on the total weight of the unit dose.

Suitably, the feed additive composition or feed supplement composition comprises one or more of: a flavouring, a sweetener, and a pigment.

The number of unit doses of the feed additive composition administered will depend on the overall dose to be administered to the animal, e.g. equid. For example, if an overall dose of at least 80 mg of lactoperoxidase and 80 mg of iodide salt is desired, and a unit dose the feed additive composition comprises 8 mg of lactoperoxidase and 8 mg of iodide salt, then 10 unit doses of the feed additive composition will need to be administered to achieve the desired overall dose (of 80 mg LPO and 80 mg iodide salt, e.g. KI).

Optionally, a unit dose of the feed additive composition comprise lactoperoxidase present in an amount of from about 8 mg to about 12 mg, and in an amount of from about 0.5 wt % to about 5 wt % based on the total weight of the unit dose, the iodide salt is potassium iodide, and is present in an amount of from about 8 mg to about 12 mg, and in an amount of from about 0.5 wt % to about 5 wt % based on the total weight of the unit dose, and wherein said composition comprises optionally comprises vitamin C, and optionally comprises zinc oxide, and at least 6 unit doses are administered on a daily basis, optionally at least 8 unit doses are administered on a daily basis, preferably at least 10 unit doses are administered on a daily basis.

The present invention provides a composition, such as a pharmaceutical composition for use in treating watery mouth disease in lambs, said composition comprising lactoperoxidase, an iodide salt, and a pharmaceutically acceptable carrier and/or excipient, wherein the composition does not comprise a peroxide, or a source of peroxide, and wherein the composition does not comprise a thiocyanate or source of thiocyanate.

The composition may comprise lactoperoxidase and iodide salt in a weight ratio of from 1:10 to 10:1, preferably, from 1:3 to 3:1, most preferably from 1:1.3 to 1.3:1.

The iodide salt may for example be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

Suitably, the treatment (of WMD in lambs) comprises administration of at least 8 mg lactoperoxidase, and at least 0.048 mmol iodide salt to the lamb. Preferably, the treatment involves administration of at least 10 mg lactoperoxidase and at least 0.060 mmol iodide salt to the lamb. Suitably, the composition of the invention is administered within 48 hours of birth, preferably, within 12 hours of birth, more preferably within 6 hours of birth, most preferably within 3 hours of birth, for example within 2 hours of birth.

The treatment may comprise administration of 8 mg to 200 mg lactoperoxidase to the lamb, preferably from 8 mg to 100 mg lactoperoxidase, more preferably from 8 mg to 50 mg lactoperoxidase, such as from 8 mg to 20 mg lactoperoxidase, preferably 8 mg to 12 mg lactoperoxidase.

The treatment may comprise administration of 0.048 mmol to 1.2 mmol iodide salt to the lamb, preferably from 0.048 mmol to 0.6 mmol iodide salt, more preferably from 0.048 mmol to 0.3 mmol iodide salt, such as from 0.048 to 0.12 mmol iodide salt, preferably from 0.048 mmol to 0.072 mmol.

Suitably, the treatment comprises administration of 8 mg to 200 mg lactoperoxidase to the lamb, preferably from 8 mg to 100 mg lactoperoxidase, more preferably from 8 mg to 50 mg lactoperoxidase, such as from 8 mg to 20 mg lactoperoxidase, and the administration of administration of 0.048 mmol to 1.2 mmol iodide salt to the lamb, preferably from 0.048 mmol to 0.6 mmol iodide salt, more preferably from 0.048 mmol to 0.3 mmol iodide salt, such as from 0.048 to 0.12 mmol iodide salt, most preferably from 0.048 mmol to 0.072 mmol.

For example, the treatment comprises administration of 8 mg to 200 mg lactoperoxidase and from 0.048 mmol to 1.2 mmol iodide salt to the lamb. The treatment may comprise administration of 8 mg to 100 mg lactoperoxidase and 0.048 mmol to 0.6 mmol iodide salt to the lamb, preferably from 8 mg to 50 mg lactoperoxidase and from 0.048 mmol to 0.3 mmol iodide salt to the lamb, such as from 8 mg to 20 mg lactoperoxidase and from 0.048 mmol to 0.12 mmol iodide salt.

Disclosed herein is a composition, such as a pharmaceutically acceptable composition, for use in treating watery mouth disease in lambs, said composition comprising lactoperoxidase, an iodide salt, and a pharmaceutically acceptable carrier and/or excipient, wherein the composition does not comprise a peroxide, or a source of peroxide, and wherein the composition does not comprise a thiocyanate or source of thiocyanate, wherein the lactoperoxidase is present in an amount of at least 8 mg, and the iodide salt is present in an amount of at least 0.048 mmol.

The composition may comprise 8 mg to 200 mg lactoperoxidase to the lamb, preferably from 8 mg to 100 mg lactoperoxidase, more preferably from 8 mg to 50 mg lactoperoxidase, such as from 8 mg to 20 mg lactoperoxidase, most preferably from 8 mg to 12 mg lactoperoxidase.

The composition may comprise 0.048 mmol to 1.2 mmol iodide salt to the lamb, preferably from 0.048 mmol to 0.6 mmol iodide salt, more preferably from 0.048 mmol to 0.3 mmol iodide salt, such as from 0.048 to 0.12 mmol iodide salt, most preferably from 0.048 mmol to 0.072 mmol.

Suitably, the composition comprises 8 mg to 200 mg lactoperoxidase, and from 0.048 mmol to 1.2 mmol iodide salt, preferably from 8 mg to 100 mg lactoperoxidase and from 0.048 mmol to 0.6 mmol iodide salt, more preferably from 8 mg to 50 mg lactoperoxidase and 0.048 mmol to 0.3 mmol iodide salt, such as from 8 mg to 20 mg lactoperoxidase and from 0.048 mmol to 0.12 mmol iodide salt.

The composition for use is suitably administered within 48 hours of birth of the lamb, preferably within 12 hours of birth, more preferably within 6 hours of birth, most preferably within 3 hours of birth.

Thus, the present invention also provides for a method of treating watery mouth disease in a lamb, comprising administering to lambs a composition as disclosed herein, preferably, within 48 hours of birth of the lamb.

The composition may be provided in a unit dosage form, preferably a solid dosage form, for example in tablet form, or a pulverulent form, such as a powder form. It will be appreciated that the number of unit doses to be administered is determined by the desired treatment amount. E.g. in order to deliver a treatment of 8 mg LPO and 8 mg KI, a single unit dose comprising 8 mg LPO and 8 mg KI would need to be administered, in order to deliver a treatment of 16 mg LPO and 16 mg KI, two unit doses each comprising 8 mg LPO and 8 mg KI would need to be administered.

The lactoperoxidase may be present in an amount of from 0.5 mg to 200 mg, such as from 1 mg to 150 mg, preferably from 1 mg to 100 mg. For example, a unit dose of the pharmaceutical composition may comprise lactoperoxidase in an amount of from 0.5 mg to 200 mg, such as from 1 mg to 150 mg, preferably from 1 mg to 100 mg.

The iodide salt may be present in an amount of from 0.5 mg to 200 mg, such as from 1 mg to 100 mg, preferably from 5 mg to 50 mg, more preferably from 8 mg to 20 mg, such as from 8 mg to 12 mg. For example, a unit dose of the pharmaceutical composition may comprise iodide salt in an amount of from 0.5 mg to 200 mg, such as from 1 mg to 100 mg, preferably from 5 mg to 50 mg, more preferably from 8 mg to 20 mg, such as from 8 mg to 12 mg.

The lactoperoxidase may be present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the composition.

The iodide salt, preferably potassium iodide, is present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the composition.

Preferably, the composition is formulated for oral administration. Preferably, the composition is formulated as a tablet.

Suitably, the treatment involves administration of the pharmaceutical composition within 48 hours of birth, preferably within 12 hours of birth, most preferably within 6 hours of birth.

Preferably, the composition comprises from 8 to 12 mg lactoperoxidase, and from 8 to 12 mg of an iodide salt.

Suitably, the composition does not further comprise an oxidising agent such as an inorganic oxidising agent, for example periodic acid or a salt thereof.

Suitably, the present invention provides a composition, such as a pharmaceutical composition for use in treating watery mouth disease in lambs, said composition comprising lactoperoxidase, an iodide salt, and a pharmaceutically acceptable carrier and/or excipient, wherein the iodide salt is preferably sodium iodide or potassium iodide, and wherein the lactoperoxidase is present in an amount of from 8 to 20 mg, preferably 8 to 12 mg, and wherein the iodide salt is present in an amount of from 0.048 mmol to 0.12 mmol, preferably 0.048 mmol to 0.072 mmol, wherein the composition does not comprise a peroxide, or a source of peroxide, and wherein the composition does not comprise a thiocyanate or source of thiocyanate.

For example, the present invention provides a composition, such as a pharmaceutical composition for use in treating watery mouth disease in lambs, said composition comprising lactoperoxidase, potassium iodide, and a pharmaceutically acceptable carrier and/or excipient, wherein the lactoperoxidase is present in an amount of from 8 to 20 mg, preferably 8 to 12 mg, and wherein the potassium iodide is present in an amount of from 8 mg to 20 mg, preferably 8 mg to 12 mg, wherein the composition does not comprise a peroxide, or a source of peroxide, and wherein the composition does not comprise a thiocyanate or source of thiocyanate.

Optionally, the composition is administered within 48 hours of birth, preferably within 12 hours of birth, most preferably within 6 hours of birth.

The present invention also provides a pharmaceutical composition for use in treating diarrhea or scour in pigs, said composition comprising lactoperoxidase, an iodide salt, and a pharmaceutically acceptable carrier and/or excipient, wherein the composition does not comprise a peroxide, or a source of peroxide, and wherein the composition does not comprise a thiocyanate or source of thiocyanate. The pigs may have colibacillosis.

The pharmaceutical composition may comprise lactoperoxidase and iodide salt in a weight ratio of from 1:10 to 10:1, preferably, from 1:3 to 3:1, most preferably from 1:1.3 to 1.3:1, such as about 1:1.

The iodide salt may for example be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The pharmaceutical composition may be provided in a unit dosage form, preferably a solid dosage form, for example a pulverulent form, such as a powder form.

The treatment suitably involves the administration of at least 8 mg lactoperoxidase, and at least 0.048 mmol iodide salt to the pig on a daily basis (following weaning). Preferably, the treatment involves administration of at least 10 mg lactoperoxidase and at least 0.060 mmol iodide salt to the pig on a daily basis. Preferably, the treatment involves administration of at least 20 mg lactoperoxidase and at least 0.12 mmol iodide salt to the pig on a daily basis. Suitably, the composition of the invention is administered on a daily basis for 7 days, optionally for 14 days following weaning (i.e. once the pig is no longer suckling).

For example, the treatment may comprise administration of 10 mg to 200 mg of lactoperoxidase on a daily basis, for example, administration of 10 mg to 100 mg, preferably 10 mg to 50 mg on a daily basis. E.g. daily following weaning from day 1 to day 7, or from day 1 to day 14.

For example, the treatment may comprise administration of 0.006 mmol to 1.2 mmol of iodide salt on a daily basis, for example, administration of 0.006 mmol to 0.6 mmol, preferably 0.006 mmol to 0.3 mmol on a daily basis. E.g. daily following weaning from day 1 to day 7, or from day 1 to day.

Preferably, the composition is formulated for oral administration. Preferably, the composition is formulated as a powder.

Suitably, the composition is administered to post weaning pigs i.e. once the pigs are no longer suckling.

Suitably, the treatment involves administration of the composition to the pigs that are at least 28 days old.

Suitably, the treatment involves administration of the composition to the pigs on a daily basis. Preferably, the treatment involves administration of pharmaceutical composition to pigs on a daily basis for at least 14 days.

Preferably, the composition comprises from 8 to 50 mg lactoperoxidase, and from 8 to 50 mg of potassium iodide. More preferably from 10 to 40 mg lactoperoxidase, and from 10 to 40 mg of potassium iodide.

The composition may be provided in a unit dosage form. The unit dosage form may be a solid dosage form e.g. a tablet or powder, or a liquid dosage form including a suspension dosage form. Preferably, the unit dosage form is a powder or liquid dosage form, which advantageously can be added to the pigs feed/water, thereby making administration easier than direct administration.

The unit dose of the composition for use in treating diarrhea or scour in pigs suitably comprises lactoperoxidase in an amount of from 0.5 mg to 200 mg, such as from 1 mg to 100 mg, preferably from 8 mg to 50 mg.

The unit dose of the composition for use in treating diarrhea or scour in pigs suitably comprises iodide salt present in an amount of from 0.003 mmol to 1.2 mmol, such as from 0.006 mmol mg to 0.6 mmol, preferably from 0.048 mmol to 0.3 mmol.

Suitably the unit dose of the composition for use in treating diarrhea or scour in pigs comprises lactoperoxidase in an amount of from 0.5 mg to 200 mg, and iodide salt present in an amount of from 0.003 mmol to 1.2 mmol. For example, the unit dose of the composition for use comprises lactoperoxidase in an amount of from 1 mg to 100 mg, and iodide salt present in an amount of from 0.006 mmol mg to 0.6 mmol. Preferably, the unit dose of the composition for use comprises lactoperoxidase in an amount of from 8 mg to 50 mg, and iodide salt present in an amount of from 0.048 mmol mg to 0.3 mmol.

It will be appreciated that the number of unit doses to be administered is determined by the desired treatment amount. E.g. in order to deliver a treatment of 8 mg LPO and 8 mg KI, a single unit dose comprising 8 mg LPO and 8 mg KI would need to be administered, in order to deliver a treatment of 16 mg LPO and 16 mg KI, two unit doses each comprising 8 mg LPO and 8 mg KI would need to be administered. In order to deliver a (daily) treatment dose of 20 mg of LPO and 20 mg KI, a single unit dose comprising 20 mg of LPO and 20 mg KI would need to be administered (per day of treatment).

Suitably, the composition does not further comprise an oxidising agent such as an inorganic oxidising agent, for example periodic acid or a salt thereof.

Suitably, the composition is administered to pigs post weaning (e.g. from at least 28 days old) on a daily basis, for at least 7 days, preferably at least 14 days.

The present invention also provides a composition, such as a pharmaceutical composition, for use in treating diarrhea or scour in bovine calves, preferably dairy bovine calves, said composition comprising lactoperoxidase, an iodide salt, and a pharmaceutically acceptable carrier and/or excipient, wherein the composition does not comprise a peroxide, or a source of peroxide, and wherein the composition does not comprise a thiocyanate or source of thiocyanate.

The composition may comprise lactoperoxidase and iodide salt in a weight ratio of from 1:10 to 10:1, preferably, from 1:3 to 3:1, most preferably from 1:1.3 to 1.3:1, such as about 1:1.

The iodide salt may for example be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The treatment suitably involves administration of at least 8 mg lactoperoxidase, and at least 0.048 mmol iodide salt to the calf on a daily basis. Preferably, the treatment involves administration of at least 10 mg lactoperoxidase and at least 0.060 mmol iodide salt to the calf on a daily basis. Suitably, the composition of the invention is administered from the first day of the calf's life to the seventh (day 1 to day 7), preferably from day 1 to day 30, more preferably from day 1 to day 60.

For example, the treatment may comprise administration of 10 mg to 200 mg of lactoperoxidase on a daily basis, for example, administration of 10 mg to 100 mg, preferably 10 mg to 50 mg on a daily basis. E.g. from day 1 to day 7, or from day 1 to day 30, or from day 1 to day 60.

For example, the treatment may comprise administration of 0.006 mmol to 1.2 mmol of iodide salt on a daily basis, for example, administration of 0.006 mmol to 0.6 mmol, preferably 0.006 mmol to 0.3 mmol on a daily basis. E.g. from day 1 to day 7, or from day 1 to day 30, or from day 1 to day 60.

The pharmaceutical composition may be provided in a unit dosage form. The unit dosage form may be a solid dosage form e.g. a tablet or powder, or a liquid dosage form including a suspension dosage form. Preferably, the unit dosage form is a powder or liquid dosage form, which advantageously can be added to the calves milk, thereby making administration easier than direct administration.

The unit dose of the composition for use may comprise lactoperoxidase in an amount of from 0.5 mg to 200 mg, such as from 1 mg to 100 mg, preferably from 8 mg to 50 mg, more preferably from 8 mg to 20 mg lactoperoxidase.

The unit dose of the composition for use may comprise iodide salt present in an amount of from 0.003 mmol to 1.2 mmol, such as from 0.006 mmol mg to 0.6 mmol, preferably from 0.048 mmol to 0.3 mmol, more preferably from 0.048 mmol to 0.12 mmol iodide salt.

Suitably, the unit dose comprises lactoperoxidase in an amount of from 8 mg to 20 mg, and an iodide salt in an amount of from 0.048 mmol to 0.3 mmol. For example, a unit dose may comprise lactoperoxidase in an amount of from 8 mg to 20 mg and potassium iodide in an amount of from 8 mg to 20 mg.

It will be appreciated that the number of unit doses to be administered is determined by the desired treatment amount. E.g. in order to deliver a treatment of 8 mg LPO and 8 mg KI, a single unit dose comprising 8 mg LPO and 8 mg KI would need to be administered, in order to deliver a treatment of 16 mg LPO and 16 mg KI, two unit doses each comprising 8 mg LPO and 8 mg KI would need to be administered.

Suitably, the composition does not further comprise an oxidising agent such as an inorganic oxidising agent, for example periodic acid or a salt thereof.

Suitably, the composition is administered to bovine calves, preferably dairy bovine calves once daily, for example, once daily for the first 7 days of their lives, preferably, for the first 30 days of their lives, more preferably once daily for the first 60 days of their lives.

Suitably, the treatment involves administration of the composition to bovine calves on a daily basis. Preferably, the treatment involves administration of composition to bovine calves on a daily basis from 1 day old to 7 days old, preferably from 1 day old to 30 days old, more preferably, once daily from 1 day old to 60 days old.

In a particularly preferred embodiment, the composition for use in treating diarrhea or scour in dairy bovine calves comprises from 8 to 12 mg lactoperoxidase, and from 8 to 12 mg of potassium iodide.

The present invention further provides a pharmaceutical composition comprising lactoperoxidase, an iodide salt, and a pharmaceutically acceptable carrier and/or excipient, wherein the composition does not comprise a peroxide, or a source of peroxide, and wherein the composition does not comprise a thiocyanate or source of thiocyanate for use in the treatment or prevention of a gastrointestinal bacterial infection in a mammal.

The pharmaceutical composition may comprise lactoperoxidase and iodide salt in a weight ratio of from 1:10 to 10:1, preferably, from 1:3 to 3:1, most preferably from 1:1.3 to 1.3:1, such as about 1:1.

The iodide salt may for example be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

The pharmaceutical composition may be provided in a unit dosage form, preferably a solid dosage form, for example in tablet form, or a pulverulent form, such as a powder form.

The lactoperoxidase may be present in an amount of from 0.5 mg to 200 mg, such as from 1 mg to 150 mg, preferably from 1 mg to 100 mg. For example, a unit dose of the pharmaceutical composition may comprise lactoperoxidase in an amount of from 0.5 mg to 200 mg, such as from 1 mg to 150 mg, preferably from 1 mg to 100 mg.

The iodide salt may be present in an amount of from 0.003 mmol to 1.2 mmol, such as from 0.006 mmol to 0.6 mmol, preferably from 0.03 mmol to 0.3 mmol, more preferably from 0.048 mmol to 0.12 mmol, such as from 0.048 mmol to 0.072 mmol.

The iodide salt may be present in an amount of from 0.5 mg to 200 mg, such as from 1 mg to 100 mg, preferably from 5 mg to 50 mg, more preferably from 8 mg to 20 mg, such as from 8 mg to 12 mg. For example, a unit dose of the pharmaceutical composition may comprise iodide salt in an amount of from 0.5 mg to 200 mg, such as from 1 mg to 100 mg, preferably from 5 mg to 50 mg, more preferably from 8 mg to 20 mg, such as from 8 mg to 12 mg.

The lactoperoxidase may be present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the composition.

The iodide salt, preferably potassium iodide, is present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the composition.

Suitably, the composition does not further comprise an oxidising agent such as an inorganic oxidising agent, for example periodic acid or a salt thereof.

The composition may be formulated for oral administration.

The bacterial infection may be an enteric bacterial infection.

The bacterial infection may be an *E. coli* or *Salmonella* infection or Streptococcal infection, e.g. *Streptococcus* equinus.

The mammal may for example be a sheep, pig, horse, cat, dog or human.

Suitably, the mammal is a monogastric mammal.

The mammal may be a lamb suffering from an *E. coli* infection, for example, the lamb may be suffering from watery mouth disease.

The mammal may be a pig. The pig may for example have an *E. coli* infection. The pig may have an enteric *E. coli* infection.

The mammal may be a horse. The horse may for example have an *E. coli* infection, and/or an *S. equinus* infection. The horse may be suffering from EGUS, e.g. EGSD and/or EGGD.

In a still further aspect, the present invention provides a feed additive or dietary supplement composition comprising:
lactoperoxidase, and an iodide salt, wherein the composition does not comprise a peroxide or a source of peroxide, and wherein the composition does not comprise a thiocyanate or source of thiocyanate.

In a yet still further aspect, the present invention provides for animal feed comprising the feed additive or dietary supplement composition described herein.

In a still further aspect the present invention provides, the composition as described herein for use in treating stomach ulcers, particularly stomach ulcers in dogs, cats and equids, such as horses.

The present disclosure also provides a composition, such as a pharmaceutical composition, for oral administration comprising: lactoperoxidase, an iodide salt, and a pharmaceutically acceptable carrier and/or excipient, wherein the composition does not comprise a peroxide or a source of peroxide; and wherein the composition does not comprise thiocyanate, or a source of thiocyanate; wherein the weight ratio of the lactoperoxidase to the iodide salt is in the range of from 1:1.3 to 1.3:1.

The iodide salt may be selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

Suitably, the composition does not further comprise an oxidising agent such as an inorganic acid, for example, periodic acid or a salt thereof.

The composition may be formulated as a solid dose, such as a tablet or powder, or as a liquid dose, such as a suspension.

Preferably the composition comprises two or more excipients. For example, the composition may comprise two or more of magnesium stearate, lactose, dextrose, microcrystalline cellulose, starch (corn), silica (silicon dioxide), titanium dioxide, zinc oxide, colostrum, hydroxypropyl methyl cellulose, stearic acid, sodium starch glycolate, gelatin, talc, sucrose, calcium stearate, and povidone. For example, the pharmaceutical composition may comprise magnesium stearate, microcrystalline cellulose, and colostrum. Optionally, the composition further comprises zinc oxide.

Suitably, the composition comprises one or more of: a flavouring, a sweetener, and a pigment.

The lactoperoxidase may be present in an amount of from 0.5 mg to 200 mg, such as from 1 mg to 150 mg, preferably from 1 mg to 100 mg.

The iodide salt may be present in an amount of from 0.003 mmol to 1.2 mmol, such as from 0.006 mmol to 1.2 mmol, such as from 0.006 mmol to 0.9 mmol, preferably from 0.006 mmol to 0.6 mmol. For example, the iodide salt may be present in an amount of from 0.5 mg to 200 mg, such as from 1 mg to 150 mg, preferably from 1 mg to 100 mg.

The composition be formulated as a unit dose. Suitably, one or more unit doses of the composition may be administered.

Suitably, a unit dose of the composition may comprise 5 to 20 mg lactoperoxidase, preferably, 8 to 15 mg lactoperoxidase, more preferably, 8 to 12 mg lactoperoxidase.

Suitably, a unit dose of the composition may comprise 0.03 mmol to 0.12 mmol iodide salt, preferably, 0.048 mmol to 0.09 mmol iodide salt, more preferably, 0.048 mmol to 0.072 mmol iodide salt.

For example, a unit dose of the composition may comprise 5 mg to 20 mg iodide salt, preferably, 8 mg to 15 mg iodide salt, more preferably, 8 mg to 12 mg iodide salt.

Suitably, a unit dose of the composition comprises 5 to 20 mg lactoperoxidase, preferably, 8 to 15 mg lactoperoxidase, more preferably, 8 to 12 mg lactoperoxidase, and 0.03 mmol to 0.12 mmol iodide salt, preferably, 0.048 mmol to 0.09 mmol iodide salt, more preferably, 0.048 mmol to 0.072 mmol iodide salt.

The lactoperoxidase may be present in the unit dose in an amount of from about 0.5 to about 5 wt %, preferably from about 1 wt % to about 2 wt %, more preferably from about 1 wt % to about 1.5 wt % based on the total weight of the unit dose.

The iodide salt may be present in the unit dose in an amount of from about 0.5 to about 5 wt %, preferably from about 1 wt % to about 2 wt %, more preferably from about 1 wt % to about 1.5 wt % based on the total weight of the unit dose.

The composition for oral administration may be administered as a plurality of unit doses. Suitably, the composition may be administered as a plurality of unit doses on a daily basis.

It will be appreciated that the number of unit doses to be administered is determined by the overall treatment to be delivered.

Definitions

Before further description, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "pharmaceutically acceptable carrier" or "pharmaceutically acceptable excipient" as used herein refers to any of the following: solvents, dispersion media, coatings, isotonic and absorption delaying agents, with the proviso that they are compatible with pharmaceutical administration. The use of carriers and excipients for pharmaceutically active substances is well known to those skilled in the art. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatine; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) water; and (22) other non-toxic compatible substances employed in pharmaceutical formulations.

Furthermore, the compositions may further comprise other active compounds providing supplemental, additional, or enhanced therapeutic functions.

The term "pharmaceutical composition" as used herein refers to a composition comprising lactoperoxidase and an iodide salt as disclosed herein formulated together with one or more pharmaceutically acceptable carriers, wherein the composition does not comprise hydrogen peroxide or a source of hydrogen peroxide.

The compositions of the invention are to be administered orally, and as such they may be formulated as tablets, capsules, granules, powders, syrups, suspensions, liquids, effervescent tablets etc. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

Compositions of the present invention may include wetting agents, emulsifiers and lubricants, such as sodium lauryl sulfate and magnesium stearate, as well as colouring agents, release agents, coating agents, sweetening, flavouring and perfuming agents, preservatives and antioxidants may be present in the formulated agents.

Formulations of the compounds and pharmaceutical compositions of the invention, suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (a) fillers or extenders, e.g. sucrose, glucose, mannitol, starches, lactose, and/or silicic acid; (b) binders, e.g. carboxymethylcellulose, alginates, gelatin, polyvinyl pyrrolidone, sucrose and/or acacia; (c) humectants, e.g. glycerol; (d) disintegrating agents, e.g. agar-agar, calcium carbonate, potato or tapioca starch, alginic acid, certain silicates, and sodium carbonate; (e) solution retarding agents, e.g. paraffin; (f) absorption accelerators, e.g. quaternary ammonium compounds; (g) wetting agents, e.g. acetyl alcohol and glycerol monostearate; (h) absorbents, e.g. kaolin and bentonite clay; (i) lubricants, e.g. talc, calcium stearate, magnesium stearate, solid polyethylene glycols, sodium lauryl sulfate, and mixtures thereof; and (j) colouring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds.

A tablet may be made by compression or moulding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Moulded tablets may be made by moulding in a suitable machine a mixture of the subject composition moistened with an inert liquid diluent. Tablets, and other solid dosage forms, such as film coated tablets or sugar coated tablets, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps.

Except where indicated otherwise, the order of steps or order for performing certain actions are immaterial so long as the invention remains operable. Moreover, unless otherwise noted, two or more steps or actions may be conducted simultaneously.

DETAILED DESCRIPTION

As outlined above, the present invention provides a pharmaceutical composition, combination, and/or feed additive/dietary supplement for use in treating equine gastric ulcer syndrome, said composition comprising: lactoperoxidase, an iodide salt, and a pharmaceutically acceptable carrier and/or excipient. Suitably, the composition does not comprise a peroxide, or a source of peroxide, and wherein the composition does not comprise thiocyanate or a source of thiocyanate. Optionally, the composition does not further comprise an oxidising agent such as an inorganic oxidising agent, for example periodic acid or a salt thereof. Also described is a method of treating equine gastric ulcer syndrome comprising administering to an equid (in need thereof) a composition as described herein comprising lactoperoxidase, an iodide salt and a pharmaceutically acceptable carrier and/or excipient.

Further provided is a pharmaceutical composition, combination, and/or feed additive/dietary supplement for use in treating watery mouth disease in lambs, said composition comprising: lactoperoxidase, an iodide salt, and a pharmaceutically acceptable carrier and/or excipient. The composition does not comprise a peroxide, or a source of peroxide, and the composition does not comprise thiocyanate or a source of thiocyanate. Suitably, the composition does not further comprise an oxidising agent such as an inorganic oxidising agent, for example periodic acid or a salt thereof. Also described is a method of treating watery mouth disease in lambs comprising administering to a lamb (in need thereof) a composition as described herein comprising lactoperoxidase, an iodide salt and a pharmaceutically acceptable carrier and/or excipient.

Also provided is a pharmaceutical composition, combination, and/or feed additive/dietary supplement for use in treating diarrhea or scour in pigs, said composition comprising: lactoperoxidase, an iodide salt, and a pharmaceutically acceptable carrier and/or excipient. The composition does not comprise a peroxide, or a source of peroxide, and the composition does not comprise thiocyanate or a source of thiocyanate. Suitably, the composition does not further comprise an oxidising agent such as an inorganic oxidising agent, for example periodic acid or a salt thereof. Suitably, the pigs have colibacillosis. Also described is a method of treating diarrhea or scour in pigs comprising administering to a pig (suitably, a newly weaned pig (e.g. 28 day old, no longer suckling, in need thereof) a composition as described herein comprising lactoperoxidase, an iodide salt and a pharmaceutically acceptable carrier and/or excipient.

Also provided is a pharmaceutical composition, combination, and/or feed additive/dietary supplement for use in treating diarrhea or scour in bovine calves preferably dairy bovine calves, said composition comprising: lactoperoxidase, an iodide salt, and a pharmaceutically acceptable carrier and/or excipient. The composition does not comprise a peroxide, or a source of peroxide, and the composition does not comprise thiocyanate or a source of thiocyanate. Suitably, the composition does not further comprise an oxidising agent such as an inorganic oxidising agent, for example periodic acid or a salt thereof. Also disclosed is a method of treating diarrhea or scour in bovine calves preferably dairy bovine calves, comprising administering to a calf in need thereof a composition as described herein comprising: lactoperoxidase, an iodide salt, and a pharmaceutically acceptable carrier and/or excipient.

Furthermore, the present invention provides a pharmaceutical composition, combination, and/or feed additive/dietary supplement comprising: lactoperoxidase, an iodide salt, and a pharmaceutically acceptable carrier and/or excipient, wherein the composition does not comprise a peroxide, or a source of peroxide, and wherein the composition does not comprise thiocyanate or a source of thiocyanate. Suitably, the composition does not further comprise an oxidising agent such as an inorganic oxidising agent, for example periodic acid or a salt thereof. The composition is useful for treating, preventing, reducing the impact of a gastrointestinal bacterial infection in a mammal, such as horses, lambs, pigs, bovine calves, cats, dogs and humans. Suitably, the gastrointestinal bacterial infection is an *E. coli* or *Streptococcus* infection. The compositions of the invention may be used for prophylactic treatment of a mammal.

Despite the utility of the lactoperoxidase system for preserving milk, and in certain other applications, such as in mouthwash and disinfectants, the use of lactoperoxidase as a therapeutic in mammals is limited, particularly in monogastric mammals. This is owed in part to the requirement of hydrogen peroxide, or a source of peroxide or hydrogen peroxide in order for the lactoperoxidase system to function.

As discussed above, the lactoperoxide system involves a combination of lactoperoxidase, thiocyanate ions or halide ions and hydrogen peroxide or a source of hydrogen peroxide. A major hindrance to the widespread uptake of the lactoperoxidase system as an antimicrobial treatment is the need for hydrogen peroxide.

Hydrogen peroxide is toxic to mammalian cells. It has three major mechanisms for causing toxicity: corrosive damage, oxygen gas formation, and lipid peroxidation. High concentrations of hydrogen peroxide are caustic and can cause tissue damage. Ingestion of hydrogen peroxide can result in the production of large amounts of oxygen as a by-product of hydrogen peroxide breakdown. This oxygen can enter the blood stream where venous or arterial gas embolism may occur. There may also be a direct cytotoxic effect via lipid peroxidation, which can cause tissue damage. Hydrogen peroxide produces oxygen free radicals, and these have considerable physiological and pathological significance. Cell culture studies have reported that hydrogen peroxide is cytotoxic at concentrations ranging from 0.05-0.58 mmol/L (Rubin, R. and J. Farber (1984). "Mechanisms of the killing of cultured hepatocytes by hydrogen peroxide." Arch Biochem Biophys 228: 450-459; Ramp, W., R. Arnold, R. JE and J. Yancey (1987). High concentrations of hydrogen peroxide can compromise cell viability and decrease cell proliferation.

Advantageously, the present invention does not require exogenous hydrogen peroxide or another exogenous source of hydrogen peroxide. The compositions of the invention do not comprise a peroxide, or a source of peroxide. For example, the compositions do not comprise hydrogen peroxide, or a source of hydrogen peroxide. For example, the compositions do not comprise an oxidase enzyme, such as glucose oxidase, which leads to the production of a peroxide, such as hydrogen peroxide. The compositions of the invention do not further comprise an oxidising agent, such as an inorganic oxidising agent, such as periodic acid or a salt thereof.

Several bacterial strains produce hydrogen peroxide for example to inhibit the growth of other microorganisms. Bacterial production of hydrogen peroxide generally occurs under aerobic conditions.

There are many regions of the mammalian body where microorganisms are present which may produce hydrogen peroxide. While some regions are aerobic in nature and so allow appreciable levels of hydrogen peroxide to accumulate e.g. hydrogen peroxide production by *Streptococcus oralis* in the oral cavity (Erttmann, S. and N. Gekara (2019) "Hydrogen peroxide release by bacteria suppresses inflammasome-dependent innate immunity" Nature Communications 10: 3493), for many regions of the body where bacteria may be found, anaerobic conditions prevail greatly reducing the ability for hydrogen peroxide production and accumulation. This is particularly the case in the stomach of mammals.

For example, Fonty et al. (Fonty, G., P. Gouet, J.-P. Jouany & J.-P. Senaud (1987) "Establishment of the microflora and anaerobic fungi in the rumen of lambs" Journal of General Microbiology 133: 1835-1843) studied the development of the microbiome in lambs and sheep from birth. From birth to age 2 days, the lamb stomach was predominantly colonised by strict anaerobes, with bacterial levels of 10(9) cfu/ml seen. Over the course of the first week of life, the numbers of strict anaerobes increased, while total counts of aerobic and facultatively anaerobic bacteria were 10-100 times lower.

Swords et al. (Swords, W. E.; Wu, C. C.; Champlin, F. R.; Buddington, R. K. Postnatal changes in selected bacterial groups of the pig colonic microflora. Biol. Neon. 1993, 63, 191-200.) studied the microbiome of new-born piglets and noted that numbers of aerobic bacteria increased for the first week of life, their numbers being significantly lower than anaerobic bacteria during this period.

The literature therefore teaches that such environments would not be optimum for microbially-mediated hydrogen peroxide production.

The invention will be more readily appreciated by a review of the examples which follow.

Lactoperoxidase is an enzyme whose activity is impacted by many variables including pH. Lactoperoxidase has optimal activity at pH 6.0, with an activity range of from pH 4.5 to pH 6.5. Outside of this range the activity of the enzyme shall be greatly reduced, and as such the ability of the lactoperoxidase system (lactoperoxidase, hydrogen peroxide and thiocyanate/iodide) to oxidise thiocyanate or halide anions such as iodide outside of the aforementioned range shall be reduced.

Stomach pH is controlled by secretion of hydrochloric acid from gastric mucosa, which often leads to the stomach environment of various mammals having pH below 4.5 i.e. outside the optimal range for lactoperoxidase enzymatic activity.

The lactoperoxidase system has been demonstrated to be an effective antimicrobial agent against *E. coli*, however this effect is only seen under specific conditions. Earnshaw et al., (Earnshaw R G, Banks J G, Francotte C, Defrise D. Inhibition of *Salmonella typhimurium* and *E. coli* in an Infant Milk Formula by an Activated Lactoperoxidase System. J Food Prot. 1990 February; 53(2):170-172.) demonstrated that in an infant milk formula matrix use of the lactoperoxidase system caused an extension of the lag phase in *E. coli* before exponential growth was seen. Similarly, García-Graells et al., (García-Graells C, Valckx C, Michiels C W. Inactivation of *Escherichia coli* and *Listeria innocua* in milk by combined treatment with high hydrostatic pressure and the lactoperoxidase system. Appl Environ Microbiol. 2000; 66(10):4173-4179) showed that treatment of 4 different *E. coli* strains with the LPO system resulted in a bacteriostatic effect, with no bactericidal effects seen. Adamson and Carlsson (1982) (Lactoperoxidase and thiocyanate protect bacteria from hydrogen peroxide. Infection and Immunity. 1982, 35:1, 20-24) showed that *E. coli* was not killed by the lactoperoxidase system, but rather a bacteriostatic effect was under anaerobic conditions with rapid regrowth of cells following removal of the lactoperoxidase system. Therefore, the literature would teach against use of the lactoperoxidase system for treatment of *E. coli* infections, particularly those in anaerobic environments.

In addition, catalase is an enzyme which catalyses the decomposition of hydrogen peroxide into water and oxygen. Catalase functions to protect against damage by reactive oxygen species. *E. coli* is a catalase-positive organism. Thus *E. coli* through its catalase acts to reduce hydrogen peroxide concentrations. Hence, it is not surprising that employing the lactoperoxidase system to combat *E. coli* has had limited success, as catalase produced by *E. coli* reduces hydrogen peroxide concentration, and therefore the ability of thiocyanate or halide ions to be oxidised is reduced.

Earnshaw et al., (Earnshaw R G, Banks J G, Francotte C, Defrise D. Inhibition of *Salmonella typhimurium* and *Escherichia coli* in an Infant Milk Formula by an Activated Lactoperoxidase System. J Food Prot. 1990 February; 53(2): 170-172.) demonstrated that use of the lactoperoxidase system utilising a constant source of hydrogen peroxide produced via glucose/glucose oxidase resulted in a bacteriostatic effect against *E. coli*, while addition of exogenous hydrogen peroxide (as Urea-Hydrogen Peroxide adduct) in addition to the glucose/glucose oxidase system resulted in a slight reduction in *E. coli* numbers before exponential growth of the organism continued. The results support the use of exogenous hydrogen peroxide in the lactoperoxidase system to oxidise thiocyanate (or halide) ions, to elicit a bacteriostatic effect. The difference in the results observed may be due to the presence of catalase produced by *E. coli*.

Notwithstanding the forgoing, the present inventors have found that compositions comprising lactoperoxidase and an iodide salt have utility in treating equine gastric ulcer syndrome. Furthermore, compositions of the invention comprising lactoperoxidase and an iodide salt, do not comprise hydrogen peroxide or a source of hydrogen peroxide. Suitably, the compositions do not further comprise thiocyanate or a source of thiocyanate, and optionally, the compositions do not comprise further oxidising agents, such as inorganic oxidising agents, for example periodic acid or a salt thereof. The compositions have utility in treating EGUS, such as EGGD and ESGD. In addition, the compositions have utility in treating watery mouth disease in lambs, and diarrhea and/or scour in pigs and calves. Furthermore, the compositions have utility in treating gastrointestinal bacterial infections in mammals. The compositions of the invention are particularly efficacious in treating equine squamous gastric disease (ESGD) and/or equine glandular gastric ulceration (EGGD) in horses, watery mouth disease in lambs, colibacillosis in pigs, and in treating gastrointestinal bacterial infections in calves. The compositions of the invention also have potential for treating other bacterial infections in mammals such as *E. coli* infections in humans, particularly in infants, and stomach ulcers in cats, dogs, bovines such as bovine calves and equids such as horses.

In one aspect the present invention provides a composition such as a pharmaceutical composition comprising: lactoperoxidase, an iodide salt and a pharmaceutically acceptable carrier and/or excipient, wherein the composition does not comprise a peroxide or a source of peroxide, and does not comprise thiocyanate or a source of thiocyanate.

Lactoperoxide can be extracted from milk, and the commercial process for production of lactoperoxide involves extraction of the enzyme from cow's milk. Lactoperoxidase is commercially available from a number of food additive companies in Europe and the USA, for example from Sigma-Aldrich. Suitably, the lactoperoxidase has comprises at least ≥200 units per mg, such as ≥1000 units per mg. For example, the lactoperoxidase may comprise ≥200 units per mg, wherein one unit will oxidize 1.0 micromole of 2,2'-azino-bis(3-ethylbenzthiazoline-6-sulfonic acid) per minute at pH 5.5 at 25 Deg C. Preferably, the lactoperoxidase may comprise ≥1000 units per mg, wherein 1000 units will oxidize 1.0 mmol of 2,2'-azino-bis(3-ethylbenzthiazoline-6-sulfonic acid) in 5 minutes at pH 6.0 and at 35 Deg C.

The compositions of the invention comprise an iodide salt, for example the compositions may include one or more iodide salts. Suitable iodide salts include sodium iodide, potassium iodide, lithium iodide, ammonium iodide, calcium iodide, caesium iodide, hydrogen iodide, rhodium iodide and combinations thereof. The compositions of the invention may comprise a single iodide salt or combinations of two or iodide salts. For example, the compositions of the invention may include a combination of two or more of sodium iodide, potassium iodide, lithium iodide, ammonium iodide, calcium iodide, caesium iodide, hydrogen iodide, and rhodium iodide.

Suitably, the ratio of lactoperoxidase and iodide salt are in a weight ratio of from 1:10 to 10:1. The weight ratio may vary for different mammals, or for example, for mammals of different size. For example, provided below are representative compositions for different animals of a specified size range. Furthermore, the weight ratio will vary depending on the iodide salt employed. Preferably the iodide salt is potassium iodide or sodium iodide. Herein amounts of iodide salt have also been expressed as mmol amounts.

The composition of the invention preferably includes one or more carriers and/or excipients. The excipients may for example include fillers, diluents, binders, suspension agents, viscosity agents, coatings, flavouring agents, disintegrants, colourants, lubricants and glidants, preservatives, sweeteners.

Suitably, the excipient includes one or more of magnesium stearate, lactose, dextrose, microcrystalline cellulose, starch (corn), silica (silicon dioxide), titanium dioxide, stearic acid, sodium starch glycolate, gelatin, talc, sucrose, calcium stearate, povidone, pregelantinized starch, croscarmellose, cellulose derivatives such as hydroxypropyl methyl cellulose, hydroxypropyl cellulose or ethylcellulose, calcium phosphate, zinc oxide, and crospovidone. Particularly preferred examples include one or more of magnesium stearate, lactose, dextrose, microcrystalline cellulose, starch (corn), silica (silicon dioxide), titanium dioxide, stearic acid, sodium starch glycolate, gelatin, talc, sucrose, calcium stearate, and povidone.

Desirably, the composition does not include greater than 5 wt % zinc oxide based on the total weight of the composition. For example, for example, a unit dose includes less than 150 mg zinc oxide. Preferably, a unit dose comprises zinc oxide in a range of from about 0.01 wt % to about 5 wt % zinc oxide, more preferably, from about 0.01 wt % to about 1 wt % zinc oxide based on the total weight of the unit dose. For example, a unit dose may comprise 1 to 10 mg zinc oxide. Suitably, a unit dose comprises zinc oxide in an amount of from 0.01 wt % to about 5 wt %, preferably from 0.01 wt % to 1 wt % based on the total weight of the composition, wherein said unit dose comprises zinc oxide in an amount of from 1 mg to 10 mg.

Other particularly useful carriers include milk powder, colostrum (for example colostrum powder), whey protein, whey protein isolate, and beta lactoglobulin. Suitably, the compositions of the invention include milk powder and/or colostrum powder.

Materials

Lactoperoxidase was isolated from bovine milk. The lactoperoxidase activity (U/mg) was greater than 1000 units ABTS activity (determined using UV-vis). 1000 units ABTS activity (U): amount of enzyme that oxidises 1 mmol of ABTS in 5 minutes at pH 6.0 and 35° C. ABTS: 2,2'-azinobis-(3-ethyl benzthiazoline-6-sulphonic acid).

Commercially available iodide salts, e.g. potassium iodide, and sodium iodide, were employed. The salts were sieved to ensure uniform particle size prior to formulating.

Commercially available excipients, carriers, flavourings, sweeteners and pigments were used directly.

EXAMPLES

Equine Gastric Ulcer Syndrome (EGUS) Equine gastric ulcer syndrome describes the development of ulcers on the inner wall of the stomach of a horse. Ulcers can vary in severity from a minor inflammation of the stomach lining through to severe ulceration and bleeding, with potentially perforating of the stomach leading to sudden death. As outlined above, EGUS is generally treated using omeprazole (a proton pump inhibitor) which blocks the production of stomach acid. Ulceration of the stomach has been divided based upon ulcer/lesion location: equine glandular gastric disease (EGGD) refers to disease of the glandular portion of the stomach, and equine squamous gastric disease (ESGD) refers to disease of the squamous portion of the stomach. Equine gastric ulcer syndrome (EGUS) refers to disease of any portion of the stomach and is the umbrella term used.

As discussed above, EGUS is considered to result from disequilibrium between mucosal aggressive factors such as hydrochloric acid, pepsin, bile acids and organic acids, and mucosal protective factors such as mucus and bicarbonate. Several factors have been implicated in causing ulceration including fasting, gastric acid clearance (gastric motility and emptying), aggressiveness of the gastric juice (acid, pepsin, bile acids, organic acids) and the process of desquamation. Fermentation by-products of carbohydrates may lead to the formation of volatile fatty acids, which perpetuate damage caused by hydrochloric acid. Bacteria present in the stomach may also play a role in onset and development of stomach ulcers. Lactic acid and volatile fatty acids (VFAs) are thought to play a role in establishment and progression of ulcers. Lactic acid is produced by certain bacteria in the horse stomach. Lactic acid is thought to increase the permeability of the stomach, enabling stomach acid to diffuse into tissue layers immediately adjacent (deep) to the stratum corneum of the non-glandular mucosa, this in turn leads to stomach ulceration and/or worsening of existing ulcers. VFAs produced by stomach bacteria may play a similar role in reducing mucosal integrity.

Several lactic acid producing bacteria are found in the horse stomach, including *Lactobacillus* and *Streptococcus*, with *Streptococcus bovis* and *Streptococcus* equinus as key lactic acid producing bacteria in the equine gastrointestinal tract, with other pathogenic bacteria including *C. perfringens* and *C. botulinum* also present. Other bacterial groups present in the stomach include those from the genera

*Pseudomonas, Prevotella, Propionibacterium, Escherichia, Legionella, Voraxella* and *Pastuerella*. Notwithstanding the foregoing, as outlined in a recent review article by Vokes et al. (Animals 2023, 13, 1261. https://doi.org/10.3390/ani13071261) the relationship between bacteria and EGUS is not clear, and the standard of care for treating EGUS is to administer omeprazole. In a recent report, it was considered that there was no support for the use of antimicrobials to treat EGGD.

Furthermore, it has been reported that treatment of EGUS with an oral antimicrobial in combination with omeprazole showed no improvement over omeprazole alone.

As outlined above, two types of gastric ulcer include squamous ulcers and glandular ulcers. Squamous ulcers occur in the upper section of the stomach, often near the junction between the squamous and glandular tissues of the stomach. Glandular ulcers occur in the lower section of the stomach when there is a breakdown of the protective mucus layer over the stomach lining.

Gastroscopy is employed to diagnose and monitor stomach ulcers. This allows for determination of the number of ulcers and their location, along with severity of the ulceration.

A standard 5-point grading system is typically employed by practitioners, this grades the gastric ulcers from 0 to 4 in both the glandular region of the stomach and the squamous (non-glandular) region of the stomach.

| Glandular Mucosa (EGGUS grading) | | Squamous Mucosa (ESGUS grading) | |
| --- | --- | --- | --- |
| Grade | Description | Grade | Description |
| 0 | Epithelial wall is intact and there is no appearance of hyperaemia. | 0 | There is no appearance of hyperkeratosis or hyperaemia and the epithelial wall is intact. |
| 1 | Areas of hyperaemia are visualised, but the mucosa is intact. | 1 | Areas of hyperkeratosis and hyperaemia are visualised, but the mucosa wall is still intact. |
| 2 | Minor, single lesions are visualised. | 2 | Minor, single lesions are visualised. |
| 3 | Large, single lesions are visualised or extensive superficial lesions. | 3 | Large, single lesions are visualised or extensive superficial lesions. |
| 4 | Areas of deep ulceration or mucosal pathology is visualised. | 4 | Extensive lesions are visualised deep to the mucosa. |

The present inventors postulated that the use of lactoperoxidase and an iodide source could be effective in treating EGUS. To evaluate the efficacy of the compositions of the present invention in the treatment of EGUS, an animal study was undertaken with 5 racehorses suffering from EGUS. Animals were treated with 70 mg LPO and 60 mg KI in tablet form once daily (trial group). The tablet also included excipients. The control horse was not given any additive (control group). Gastroscopy was carried out by a team of three people including a specialist equine veterinarian at week 0 (prior to trial commencement), week 2, week 4 and week 6. Horses were scored at these time points and clinical condition at the end of the trial was noted.

Scoring during the trial and commentary on clinical condition is summarised below:

| T0 Horse | ESGUS grade | EGGUS grade | Appetite | Weight (kg) |
| --- | --- | --- | --- | --- |
| C1 | 2 | 2 | G | 550 |
| P1 | 3 | 1 | G | 478 |
| P2 | 2 | 2 | G | 598 |
| P3 | 3 | 1 | G | 513 |
| P4 | 4 | 2 | G | 467 |

G = good

| T2 (2 weeks) Horse | ESGUS grade | EGGUS grade | Appetite | Weight (kg) |
| --- | --- | --- | --- | --- |
| C1 | 1 | N/a** | G | 550 |
| P1 | 2 | 1 | G | 487 |
| P2 | 1 | N/a** | G | 629 |
| P3 | 2 | 3 | G | 522.5 |
| P4 | 3 | 2 | G | 461 |

G = good;
N/a** = visibility obscured by food

| T4 (4 weeks) Horse | ESGUS grade | EGGUS grade | Appetite | Weight (kg) |
| --- | --- | --- | --- | --- |
| C1 | N/p | N/p | N/p | N/p |
| P | N/p* | N/p* | N/p* | N/p* |
| P2 | 1 | 1 | G | 573 |
| P3 | 2 | 0 | G | 498 |
| P4 | N/p | N/p | N/p | N/p |

G = good;
N/p = not performed;
N/p* = not performed as horse died unrelated to trial

| T6 (6 weeks) Horse | ESGUS grade | EGGUS grade | Appetite | Weight (kg) |
| --- | --- | --- | --- | --- |
| C1 | 2 | 2 | G | 556 |
| P1 | N/p* | N/p* | N/p* | N/p* |
| P2 | 2 | 0 | G | 591 |

| T6 (6 weeks) Horse | ESGUS grade | EGGUS grade | Appetite | Weight (kg) |
|---|---|---|---|---|
| P3 | 1 | 0 | G | 513 |
| P4 | 1 | 0 | G | 474 |

G = good;
N/p* = not performed as horse died unrelated to trial

In the trial cohort, two out of the three horses that completed the trial had their ulcers resolved—both with starting EGUS scores of 3 or higher (P3 & P4). The remaining horse that completed the trail (P2) was deemed to have improved, with an absence of ulceration in the glandular region of the stomach, and only minor ulceration observed in the non-glandular (squamous) region of the stomach. A final horse from the trial group died during the study, this was unrelated to the study itself. Similar to others in the trial grouping, this horse showed an improvement in EGUS scoring from week 0 to week 2.

The condition of the control horse did not improve after six weeks.

Advantageously, the composition of the invention proved effective in treating equine gastric ulcer syndrome, with improvements being observed after treatment of both squamous and glandular ulcers. Without being bound by theory, it is thought that the iodide is oxidised by endogenous oxidants in the presence of lactoperoxidase in the equine stomach, which is thought to lead to the production of oxidised iodide species, such as hypoiodite (IO—) and hypoiodous acid (HOI). These species are potent, non-specific antimicrobial agents, which may elicit their antimicrobial effect in the horse stomach, leading to a reduction in acids such as lactic acid and/or volatile fatty acids, and enable ulcer healing.

Following the above-identified preliminary trial several further trials were conducted.

EGUS Trial 2: A larger study of 26 race horses in full training was conducted. The horses were scoped on the day before trial commencement and after 5 weeks of treatment. A sub-group of eight horses were also scoped after 14 weeks. The trial involved administration of a daily dose of 66.4 mg LPO and 66.4 mg KI. The daily dose was made up with a solid oral dosage form comprising tablets. An exemplified tablet had the following composition:

| Ingredient | Mg | wt % based on the total weight of the composition/tablet |
|---|---|---|
| Potassium iodide | 8.3 | 1.38 |
| Lactoperoxidase | 8.3 | 1.38 |
| Mixture of Excipients | 583.4 | 97.24 |

Each horse received 8 tablets per day with feed. The scoping results for EGUS trial 2 are shown in the below table:

| Horse identifier | ESGD score | | |
|---|---|---|---|
| | $T_0$ | $T_{5\ weeks}$ | $T_{14\ weeks}$ |
| MH101 | 4.0 | 0.0 | 0.0 |
| MH102 | 4.0 | 1.0 | |
| MH103 | 4.0 | 0.0 | 0.0 |
| MH104 | 4.0 | 2.0 | |
| MH105 | 4.0 | 2.0 | |
| MH106 | 4.0 | 2.5 | |
| MH107 | 4.0 | 2.5 | 2.5 |
| MH108 | 3.0 | 2.0 | |
| MH109 | 4.0 | 3.0 | 2.5 |
| MH110 | 3.0 | 2.5 | 2.0 |
| MH111 | 3.0 | 1.0 | |
| MH112 | 3.0 | 2.0 | |
| MH113 | 3.0 | 1.0 | |
| MH114 | 3.0 | 2.0 | |
| MH115 | 4.0 | 2.5 | 0.0 |
| MH116 | 3.0 | 0.0 | 0.0 |
| MH117 | 4.0 | 1.0 | |
| MH118 | 3.0 | 1.5 | |
| MH119 | 4.0 | 1.0 | |
| MH120 | 2.0 | 0.0 | 0.0 |
| MH121 | 4.0 | 2.0 | |
| MH122 | 4.0 | 2.0 | |
| MH123 | 2.0 | 3.0 | 0.0 |
| MH124 | 2.0 | 3.0 | 1.0 |
| MH125 | 4.0 | 3.0 | 1.0 |
| MH126 | 3.0 | 3.0 | 0.0 |
| Average | 3.42 | 1.75 | 0.75 |
| Median | 4 | 2 | 0 |

The data shown above are for the assessment of the squamous mucosa of the trial horses i.e. ESGD/ESGUS scores. After 5 weeks a significant reduction in ulceration was observed (approx. 49%), demonstrating efficacy of the composition of the present invention for treating equine ulcer gastric syndrome. Of the 26 horses that participated in the 5 week trial, dosing was continued in a sub-group of horses up to 14 weeks. The overall average ESGD score reducing to 0.75 after 14 weeks. Furthermore, severity of ulcers reduced across the entire sub-group.

EGUS Trial 3: A study of 30 race horses in full training was conducted. The trial included 25 trial horses, and 5 control horses. The horses were scoped on the day before trial commencement and after 8 weeks of treatment. A sub-group of horses were also scoped after 16 weeks. Control horses did not receive any treatment/supplementation over the course of the trial. The trial involved administration of a daily dose of 83 mg LPO and 83 mg KI to trial horses. The daily dose was made up of a solid oral dosage form comprising the composition of the invention, in the form of tablets. Tablets employed in the trial had the following composition:

| Ingredient | Mass per tablet (mg) | wt % based on the total weight of the composition/tablet |
|---|---|---|
| Potassium iodide | 8.3 | 1.38 |
| Lactoperoxidase | 8.3 | 1.38 |
| Vitamin C | 20.0 | 3.33 |
| Silicified microcrystalline cellulose | 100 | 16.67 |
| Other excipients including apple flavouring and sorbitol sweetener | 463.4 | 77.24 |

To achieve the dose of 83 mg lactoperoxidase and 83 mg potassium iodide, 10 tablets were administered once daily.

EGUS trial 3 involved assessing ulceration in the squamous section of the stomach in all horses, and ulceration in the glandular section of the stomach was also assessed in two horses (MH007 and MH010). The ESGD scores for each of the horses is shown in the below table:

| Horse identifier | ESGD score | | |
|---|---|---|---|
| | $T_0$ | $T_{8\ weeks}$ | $T_{16\ weeks}$ |
| MH001 | 3.5 | 1.5 | |
| MH002 | 3.0 | 0.0 | 0.0 |
| MH003 | 2.0 | 1.0 | |
| MH004 | 3.0 | 3.0 | 2.0 |
| MH005 | 2.0 | 0.0 | 0.0 |
| MH006 | 2.5 | 0.5 | |
| MH007* | 4.0 | 3.0 | |
| MH008 | 3.0 | 2.0 | 0.0 |
| MH009 | 3.0 | 1.5 | |
| MH010* | 4.0 | 2.5 | |
| MH011 | 3.0 | 2.5 | |
| MH012 | 2.5 | 3.0 | |
| MH013 | 3.0 | 0.0 | 0.0 |
| MH014 | 3.0 | 0.0 | 0.0 |
| MH015 | 2.0 | 2.5 | 2.5 |
| MH016 | 2.5 | 2.5 | 1.5 |
| MH017 | 2.5 | 3.0 | |
| MH018 | 2.5 | 0.5 | |
| MH019 | 3.0 | 2.0 | 1.0 |
| MH020 | 2.0 | 2.0 | 2.0 |
| MH021 | 3.0 | 0.0 | 0.0 |
| MH022 | 4.0 | 0.0 | 0.0 |
| MH023 | 2.0 | 2.0 | |
| MH024 | 4.0 | 2.0 | 1.0 |
| MH025 | 3.5 | 2.5 | |
| Average | 2.90 | 1.58 | 0.8 |
| Median | 3.0 | 2.0 | 0.0 |
| Controls | | | |
| MH026 | 0 | | 1.5 |
| MH027 | 1.5 | | 2 |
| MH028 | 0 | | 0 |
| MH029 | 0 | | 2 |
| MH030 | 1 | | 2 |
| Average | 0.50 | | 1.50 |
| Median | 0.00 | | 2.0 |

After 8 weeks a significant reduction in ulceration was observed, with a 46% reduction in the average ESGD score. This reduction in ulceration also continued in the sub-group of trial horses, where dosing was continued for 16 weeks. The average ESGD score after 16 weeks was 0.8. In contrast, an increase in ulceration was observed in control horses over the 8 week trial period.

Three of the trial horses were also assessed for glandular ulceration:

| Horse identifier | EGGD score | |
|---|---|---|
| | $T_0$ | $T_{8\ weeks}$ |
| MH007 | 3.0 | 0 |
| MH010 | 2.0 | 0 |
| MH022 | 4.0 | 1.5 |
| Average | 3.0 | 0.5 |

Advantageously, glandular ulceration was resolved in two of the three trial horses where EGGD scores were determined, and an average reduction of over 80% was observed. This is a particularly desirable result given the standard of care for treating ESGD i.e. omeprazole has very limited efficacy in treating EGGD.

The tablets were administered with pelletized feed, and notably, including apple flavouring and sorbitol sweetener in the composition, led to preferential eating of the tablets i.e. the horses preferred the taste of the tablets to the pelletized feed.

EGUS trial 4: To further assess the utility of the composition of the invention for treating EGGD a further trial was conducted. In EGUS trial 4, 8 horses were assessed over an 8 week period. Of the 8 horses participating in the trial, 6 horses were trial horses and received a dose of 83 mg LPO and 83 mg KI per day, by way of administration of 10 tablets (each comprising 8.3 mg LPO and 8.3 mg KI plus excipients) once per day with feed, the tablets were similar to those employed in EGUS trial 3, albeit the excipient content was modified. The remaining two participating horses were control horses who were monitored over the eight-week period but did not receive any treatment. ESGD and EGGD scores were determined on the before trial commencement, after 4 weeks and after 8 weeks of the trial. The results are shown in the below table:

| | $T_0$ | | $T_{4\ weeks}$ | | $T_{8\ weeks}$ | |
|---|---|---|---|---|---|---|
| Horse Identifier | ESGD | EGGD | ESGD | EGGD | ESGD | EGGD |
| MH301 | 2.0 | 0.0 | 2.0 | 0.0 | 0.0 | 0.0 |
| MH302 | 4.0 | 0.0 | 2.0 | 0.0 | | |
| MH303 | 2.0 | 2.0 | 2.0 | 1.0 | 2.0 | 1.0 |
| MH304 | 2.0 | 1.0 | 2.0 | 1.0 | 2.0 | 1.0 |
| MH305 | 0.0 | 1.0 | 1.5 | 0.0 | 0.0 | 0.0 |
| MH306 | 3.0 | 1.0 | 2.0 | 0.0 | 2.0 | 0.0 |
| Average | 2.2 | 1.0 | 1.9 | 0.3 | 1.2 | 0.4 |
| MH307 | 0.0 | 0.0 | 0.0 | 0.0 | 1.0 | 0.0 |
| MH308 | 0.0 | 0.0 | 2.0 | 2.0 | 1.0 | 1.0 |
| average | 0.0 | 0.0 | 1.0 | 1.0 | 1.0 | 0.5 |

In trial horses, a 44% reduction in the average ESGD scores was observed after an 8 week period. Furthermore, a 60% reduction was observed in EGGD scores over the 8 week period. In EGUS trial 4, the control horses participating in the trial had no ulceration at the start of the trial, but by the end of the trial ulceration was present. Pleasingly, modification of the excipients did not alter the efficacy of the treatment.

In a further trial, EGUS trial 5, a lower daily dose of LPO and KI was evaluated in 4 horses over a 3 week period. Only the squamous section of the stomach was scoped. In EGUS trial 5 the decrease in ulceration was more limited for the lower daily dose of 41.5 mg LPO and 41.5 mg KI than was observed for the higher dose trials.

Each of the above trials were conducted on high performance race horses. Treating with at least 60 mg of LPO and at least 0.36 mmol of iodide salt proved highly effective, as did higher doses of at least 80 mg of LPO and at least 0.48 mmol of iodide salt. Treating with lower amounts, such as at least about 40 mg of LPO and at least 0.24 mmol of iodide salt is considered preferable for smaller equids, e.g. horses/ponies having a mass of less than about 500 kg, or for pleasure horses where training is less vigorous.

Advantageously, the compositions of the present invention were successful in treating both EGSD and EGGD. The compositions and methods described herein thus provide an alternative or additional treatment for EGUS to proton pump inhibitors such as omeprazole.

Watery Mouth Disease in Lambs

Watery mouth disease is a bacterial disease of newborn lambs, most commonly seen in lambs between 6 and 48 hours old. The inventors examined the efficacy of compositions comprising lactoperoxidase, an iodide salt and excipients in treating watery mouth disease in lambs. An animal study was conducted on a commercial sheep farm to determine the impact of the invention on the prevention and treatment of watery mouth disease in newborn lambs.

The experiment was run over two lambing periods, with one lambing cohort receiving the test material, and another cohort acting as a control group.

Lambs in the test group received a composition comprising 12 mg KI and 12 mg lactoperoxidase, and excipients formulated as a single tablet (400 mg tablet). The composition did not comprise thiocyanate, or a source of thiocyanate; the composition did not contain peroxide or a source of peroxide; the compositions also did not contain any inorganic oxidising agents, such as periodic acid or a salt thereof. The tablet was administered once within 2 hours of birth. No antibiotics were administered to lambs in the test group.

Mortality at 14 days post birth is summarised in the table below:

|  | Control group | Test group |
| --- | --- | --- |
| Number of new-born lambs | 1305 | 1207 |
| Incidence of Watery Mouth Disease (WMD) | 253 | 0 |
| Mortality at day 14 | 116 | 0 |

Lambs that were administered the composition of the invention in this trial did not contract watery mouth disease. While 116 lambs in the control group died, no deaths were recorded in the test grouping.

A second trial was carried out where lambs were prophylactically treated with the composition of the invention (trial group) or with spectinomycin (Spectam Scour Halt Oral Solution 50 mg/ml) (control group). The composition of the invention was administered as a single tablet, as outlined above in the first trial group. The composition comprised 10 mg KI, 12 mg lactoperoxidase and excipients, and was formulated as a tablet. As outlined above, the tablet did not contain thiocyanate or a source thereof, nor peroxide or source thereof, nor did the tablet further comprise an inorganic oxidising agent, such as periodic acid or a salt thereof.

The second trial was carried out with an indoor lambing flock of lowland ewes in Scotland. Watery Mouth Disease had a prevalence ranging between 2% and 5.5% in lambs born over the previous four years. This is within the typical range that is experienced in similar flocks. The standard management has been to administer a single 1 ml dose of Spectam Scour Halt Oral Solution, which comprises spectinomycin (as spectinomycin dihydrochloride pentahydrate) in a concentration of 50 mg/ml, as soon as possible after birth and within 48 hours of birth. Ewes and lambs are housed in individual pens for 24 to 48 hours before moving to group pens, until weather is mild enough for them to be turned out to pasture.

434 lambs were delivered in an indoor system over a four week period. Three shepherds worked in 8-hour shifts, with one shepherd administering a trial composition in tablet form (i.e. a composition of the present invention in tablet form), and the other two shepherds administering a single dose of Spectam Scour Halt Oral Solution 50 mg/ml to the control group. 282 lambs received a single dose of Spectam Scour Halt Oral Solution and 152 lambs received a single dose of the trial composition in tablet form. the occurrence of watery mouth disease was approx. 2.5% (7 lambs) in the control group, and the occurrence of watery mouth disease in the trial group was approx. 2% (3 lambs). Thus, under circumstances where watery mouth disease occurred, the efficacy of the composition of the invention was at least comparable with, if not slightly better than, prophylactic antibiotic treatment.

Advantageously, the compositions of the present invention are effective in treating and/or preventing watery mouth disease in lambs. Without being bound by theory it is thought that the iodide salt is oxidised by endogenous oxidants in the gastrointestinal tract of the lamb in the presence of lactoperoxidase, which is thought to lead to the production of oxidised iodide species, such as hypoiodite (IO—) and hypoiodous acid (HOI). These species are potent, non-specific antimicrobial agents, and are thought to kill bacteria that are implicated in watery mouth disease in newborn lambs. Advantageously, the compositions of the present invention do not comprise thiocyanate, or a source thereof, nor do they comprise peroxide or a source thereof, nor do they further comprise strong oxidising agents such as the inorganic oxidising agent, periodic acid or a salt thereof. The absence of such reactive species advantageously significantly increases the shelf life of the compositions of the invention, over traditional lactoperoxidase systems, particularly in liquid formulations.

Pig Studies

Bacterial infections in pigs may lead to diarrhea or scour. For example, $E.$ $coli$ infections in pigs may lead to colibacillosis in pigs who suffer from consequent diarrhea or scour. Post-weaning diarrhea (PWD) in pigs is commonly associated with enterotoxigenic $E.$ $coli$(ETEC), which is one of the most prevalent porcine diseases, accounting for substantial economic losses worldwide.

A trial was conducted to determine the potential impact of the compositions of the invention for controlling $E.$ $coli$ infection and improving animal health.

Piglets were weaned at 28 days of age with an average weight of 8.6±0.98 kg. At weaning (i.e. no longer suckling), litters were homogenized to a maximum of 14 pigs and assigned to either a control group (no additional feed component), to a first test group to which the composition of the invention was administered, and to a second test group to which zinc oxide was administered. Pigs were fed starter diets up until day 14 of the trial when the trial completed.

Group weight and feed intake was recorded at day 0, 7 and 14 of the experiment.

The composition of the invention comprised: 10 mg LPO and 8 mg KI and excipients. The composition was formulated as a powder. The composition was administered once daily with feed for 14 days. The powder composition did not comprise thiocyanate, or a source of thiocyanate, nor did it contain peroxide or a source of peroxide, nor did it comprise an inorganic oxidising agent, such as periodic acid or a salt thereof. Zinc oxide was administered to the second test group at a concentration of 3000 ppm i.e. 3 g/kg of feed.

| Average daily gain (g/d) and average daily feed intake at day 14 | | | |
| --- | --- | --- | --- |
|  | Control | Test 1 | Tests 2 |
| Average daily gain (g//d) day 14 | 311 | 336 | 369 |
| Average daily feed intake (g/d) day 14 | 389 | 415 | 455 |

An increased daily weight gain was seen in pigs receiving the test material, with pigs receiving test material gaining significantly more weight than the control group.

| Average body weight (kg) | | | |
|---|---|---|---|
| | Control | Test 1 | Test 2 |
| Day 0 | 8.6 | 8.5 | 8.5 |
| Day 7 | 10.0 | 10.0 | 10.1 |
| Day 14 | 12.9 | 13.2 | 13.7 |

Increased body weights were seen in pigs receiving the test material as compared to control. Pigs were offered feed ad libitum.

A further study involving 240 pigs was carried out with a higher dose of lactoperoxidase and potassium iodide. The pigs were weighed and allocated to the trail at weaning (approximately 28 days of age). Pigs were assigned to one of three groups:
  (i) positive control (PC) group—fed a standard nursery diet with 3100 ppm ZnO
  (ii) negative control (NC) group—fed a standard nursery diet (<150 ppm ZnO)
  (iii) test group—fed standard nursery diet (<150 ppm ZnO) plus composition of the invention—a single dose per day containing 20 mg LPO and 20 mg KI.

The groups were homogenized with respect to group total weight and gender profile, and each group was divided into pens, with 5 pigs per pen. As outlined above, diets (ii) and (iii) did not contain therapeutic quantities of ZnO. The pigs were weighed individually at the start of the study on day 7 and on day 14. Pigs were assessed each morning for general health, faeces was examined—to check for scour/diarrhea, and pigs per give a cleanliness score

| Health score | Cleanliness score |
|---|---|
| 0-no signs of poor health | 1-clean |
| 1-some signs of poor health | 2-some indication of faecal contamination |
| 2-clear signs of poor health | 3-contaminated with faecal material |
| 3-serious signs of poor health | 4-heavily contaminated with faecal material |

Wean weight was similar for all treatments with a start weight of approx. 7.7 kg. At the end of the 14 days, pigs fed the PC diet were heaviest with pigs and pigs fed the NC diet weighing approximately 0.8 kg less. Pigs fed the test diet (group (iii) above) had an intermediate weight, but were approximately the same weight as those in the PC diet after 7 days. The mean health score in each of the groups was similar, however, pigs in the test group had the best cleanliness score, with pigs in the positive control group having the lowest cleanliness score.

In both of the above-trials though the test group to which zinc oxide (at a concentration of 3,000 ppm (in the first trial) or 3,100 ppm (in the second trial)) was administered exhibited the greatest increase in weight, the composition of the present invention also led to increased weight in comparison to the negative control cohorts. Furthermore, the administration of high concentrations of zinc oxide (e.g. 1000 ppm or higher) to pigs as a feed additive will be prohibited in Europe once zinc oxide products marketed for such treatment that have been placed on the market prior to July 2022 are exhausted, thus suitable alternative feed additives and/or prophylactic treatments to combat colibacillosis, scour and diarrhea in pigs are required. The composition of the present invention has demonstrated efficacy as a suitable alternative to zinc oxide for preventing scour in pigs. Advantageously, the compositions of the present invention are effective in treating and/or preventing diarrhea or scour in pigs, particularly in newly weaned piglets (e.g. 28 day old pigs). Without being bound by theory it is thought that the iodide salt is oxidised by endogenous oxidants in the gastrointestinal tract of the pig in the presence of lactoperoxidase, which is thought to lead to the production of oxidised iodide species, such as hypoiodite (IO—) and hypoiodous acid (HOI). These species are potent, non-specific antimicrobial agents, and are thought to kill bacteria that cause diarrhea or scour in pigs. Advantageously, the compositions of the present invention do not comprise thiocyanate, or a source thereof, nor do they comprise peroxide or a source thereof, nor do they comprise strong oxidising agents such as the inorganic oxidising agent, periodic acid or a salt thereof. The absence of such reactive species advantageously significantly increases the shelf life of the compositions of the invention, over traditional lactoperoxidase systems.

In addition, the composition of the present invention is effective for controlling *E. coli* infection in pigs, and for example, may be used prophylactically. For example, the composition of the invention may be used to prevent diarrhea or scour in pigs, for example diarrhea or scour caused by *E. coli*. infection.

In the various aspects described above, compositions of the invention comprise lactoperoxidase and an iodide salt. The compositions of the invention have demonstrated efficacy in treating and/or preventing various conditions in different species. Representative dosing for treating different species are provided below:

Example 1

Horses (body weight approx. 500 kg): Daily dosage comprising 50 to 85 mg potassium iodide and 50 to 85 mg lactoperoxidase, e.g. 60 to 80 mg potassium iodide and 60 to 80 mg lactoperoxidase.

Preferred dosage: solid dosage, e.g. tablets.

Example 2

New-born lambs (body weight of approx. 5.5 kg): treatment of WMD with unit dose comprising 8 to 20 mg potassium iodide, and 8 to 20 mg lactoperoxidase e.g. a unit dose comprising 10 mg potassium iodide and 12 mg lactoperoxidase (e.g. administered daily).

Preferred dosage: tablet or oral suspension

Lambs may be treated prophylactically by dosing as soon as possible after birth, for example, by administering a tablet or oral suspension formulation comprising lactoperoxidase and potassium iodide. For example, within 48 hours after birth, preferably, within 24 hours after birth, more preferably, within 12 hours after birth, such as within 6 hours or 2 hours after birth.

Example 3

Piglets at weaning (body weight of approx. 5-7 kg): Treating/preventing diarrhea/scour with for example a unit dosage comprising 8 to 30 mg potassium iodide, and 8 to 30 mg lactoperoxidase e.g. a unit dose comprising 20 mg potassium iodide and 20 mg lactoperoxidase (e.g. administered daily).

Preferred dosage: dissolvable powder, effervescent tablet or liquid formulation.

Example 4

Dogs/Cats (body weight of approx. 2-50 kg): Unit dosage comprising for example 2 to 4 mg potassium iodide and 2 to 4 mg lactoperoxidase per kg of body weight, e.g. administer 2.5 mg potassium iodide and 3 mg lactoperoxide per kg of body weight.

Preferred dosage: dissolvable powder, effervescent tablet or liquid formulation.

The above dosages may for example be added to animal feed or administered directly as appropriate.

Example 5

Human infants (body weight of approx. 2-25 kg): Unit dosage comprising for example 3 to 10 mg potassium iodide, and 3 to 10 mg lactoperoxidase, e.g. 5 mg potassium iodide and 7.5 mg lactoperoxidase.

Preferred dosage: liquid formulation or suspension.

The dose may for example be administered once or twice daily for two to three consecutive days.

The compositions of the invention may comprise a carrier or excipient.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Embodiments

1. A composition, such as a pharmaceutical composition, comprising:
   lactoperoxidase, an iodide salt, and
   a pharmaceutically acceptable carrier and/or excipient,
   for use in the treatment or prevention of equine gastric ulcer syndrome, optionally wherein the equine gastric ulcer syndrome comprises equine squamous gastric disease and/or equine glandular gastric disease.

2. The composition for use of embodiment 1, wherein the composition does not comprise a peroxide, or a source of peroxide.

3. The composition for use of embodiment 1 or 2, wherein the composition does not comprise thiocyanate, or a source of thiocyanate.

4. The composition for use of any preceding embodiment wherein the lactoperoxidase and iodide salt are in a weight ratio of from 1:10 to 10:1, preferably, from 1:3 to 3:1, most preferably from 1:1.3 to 1.3:1, such as about 1:1.

5. The composition for use of any preceding embodiment, wherein the iodide salt is selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

6. The composition for use of any preceding embodiment, wherein said composition is a solid dosage form, for example in tablet form or powder form.

7. The composition for use of any one of embodiments 1 to 5, wherein said composition is a liquid dosage form, for example a suspension.

8. The composition for use of any preceding embodiment, further comprising vitamin C.

9. The composition for use of any preceding embodiment, further comprising one or more of magnesium stearate, lactose, dextrose, microcrystalline cellulose, starch (corn), silica (silicon dioxide), titanium dioxide, colostrum, zinc oxide, hydroxypropyl methyl cellulose, stearic acid, sodium starch glycolate, gelatin, talc, sucrose, calcium stearate, and povidone.

10. The composition for use of any preceding embodiment, wherein the treatment comprises administration of at least 0.24 mmol of the iodide salt, and at least 40 mg of the lactoperoxiase on a daily basis, preferably, wherein the treatment comprises administration of at least 0.36 mmol of the iodide salt and at least 60 mg of the lactoperoxidase on a daily basis, more preferably, wherein the treatment comprises administration of at least 0.48 mmol of the iodide salt and at least 80 mg of the lactoperoxidase on a daily basis.

11. The composition for use of any preceding embodiment, wherein the treatment comprises administration of from 0.24 mmol to 1.2 mmol of the iodide salt, and 40 mg to 200 mg of the lactoperoxidase to the equid on a daily basis, such as from from 0.36 mmol to 1.2 mmol of the iodide salt and from 60 mg to 200 mg of the lactoperoxidase to the equid on a daily basis, optionally from 0.48 mmol to 0.60 mmol of the iodide salt and 80 mg to 100 mg of the lactoperoxidase to the equid on a daily basis.

12. The composition for use of any preceding embodiment, wherein the treatment comprises administration of at least 40 mg of the iodide salt, and at least 40 mg of the lactoperoxidase on a daily basis, preferably wherein the treatment comprises administration of at least 60 mg of the iodide salt and at least 50 mg of the lactoperoxidase on a daily basis, for example, wherein the treatment comprises administration of at least 60 mg of the iodide salt and at least 60 mg of the lactoperoxidase on a daily basis, more preferably, wherein the treatment comprises administration of at least 80 mg of the iodide salt and at least 80 mg of the lactoperoxidase on a daily basis.

13. The composition for use of any preceding embodiment, wherein the treatment comprises administration of 40 mg to 200 mg of the iodide salt, and 40 mg to 200 mg of the lactoperoxidase to the equid on a daily basis, such as from 60 mg to 200 mg of the iodide salt and 60 mg to 200 mg of the lactoperoxidase to the equid on a daily basis, optionally from 80 mg to 100 mg of the iodide salt and 80 mg to 100 mg of the lactoperoxidase to the equid on a daily basis.

14. The composition for use of any preceding embodiment, wherein the treatment is continued for a period of at least four weeks, preferably at least 8 weeks, more preferably at least 12 weeks.

15. The composition for use of any preceding embodiment, wherein the treatment comprises administration of the composition on a daily basis at least four days per week, preferably, at least 5 days per week.

16. The composition for use of any preceding embodiment, wherein a unit dose of the composition comprises lactoperoxidase present in an amount of from 0.5 mg to 200 mg, such as from 1 mg to 100 mg, preferably from 5 mg to 50 mg, more preferably from 8 mg to 20 mg, such as from 8 mg to 12 mg.

17. The composition for use of any preceding embodiment, wherein a unit dose of the composition comprises iodide salt present in an amount of from 0.003 mmol to 1.2 mmol, such as from 0.006 mmol to 0.6 mmol, preferably from 0.030 mmol to 0.30 mmol, more preferably from 0.048 mmol to 0.12 mmol, such as from 0.048 mmol to 0.072 mmol.

18. The composition for use of any preceding embodiment, wherein a unit dose of the composition comprises iodide salt present in an amount of from 0.5 mg to 200 mg, such as from 1 mg to 100 mg, preferably from 5 mg to 50 mg, more preferably from 8 mg to 20 mg, such as from 8 mg to 12 mg.

19. The composition for use of any preceding embodiment, wherein a unit dose of the composition comprises lactoperoxidase present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the unit dose.

20. The composition for use of any preceding embodiment, wherein a unit does of the composition comprises iodide salt, is present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the unit dose.

21. The composition for use of any preceding embodiment, wherein the unit dose of the composition comprises from 5 mg to 50 mg lactoperoxidase, preferably from 8 mg to 20 mg lactoperoxidase, and wherein the unit dose of the composition comprises 0.030 mmol to 0.30 mmol iodide salt, preferably from 0.048 mmol to 0.12 mmol iodide salt.

22. The composition for use of any preceding embodiment, wherein the lactoperoxidase is present in an amount of from about 0.5 wt % to about 5 wt % based on the total weight of the unit dose, preferably from about 1 wt % to about 2 wt % based on the total weight of the unit dose, and wherein the iodide salt is present in an amount of from about 0.5 wt % to about 5 wt % based on the total weight of the unit dose, preferably from about 1 wt % to about 2 wt % based on the total weight of the unit dose.

23. The composition for use of any preceding embodiment, wherein a unit dose of the composition comprises lactoperoxidase present in an amount of from about 8 mg to about 20 mg, and in an amount of from about 0.5 wt % to about 5 wt % based on the total weight of the unit dose, and wherein the iodide salt is potassium iodide, and is present in an amount of from about 8 mg to about 20 mg, and in an amount of from about 0.5 wt % to about 5 wt % based on the total weight of the unit dose, and wherein said composition comprises optionally comprises vitamin C, and optionally comprises zinc oxide.

24. A combination for use in the treatment of equine gastric ulcer syndrome such as equine squamous gastric disease and/or equine glandular gastric disease, the combination comprising:
a lactoperoxidase; and
an iodide salt;
wherein the lactoperoxidase and iodide salt are administered sequentially or simultaneously to an equid, such as a horse or pony, in a relative weight ratio of from 1:10 to 10:1, preferably, in a relative weight ratio of from about 1:2 to 2:1, more preferably in a relative weight ratio of from about 1:1.3 to 1.3:1.

25. The combination for use of embodiment 24, wherein the treatment does not comprise a peroxide or a source of peroxide.

26. The combination for use of embodiment 24 or 25, wherein the treatment does not comprise administration of thiocyanate or a source of thiocyanate.

27. The combination for use of any one of embodiments 24 to 26, wherein the iodide salt is selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide.

28. The combination for use of any one of embodiments 24 to 27, wherein the treatment involves administration of one or more oral dosage forms.

29. The combination for use of embodiment 28, wherein the oral dosage form is a solid dosage form such as a tablet or powder, or a liquid dosage form or suspension.

30. The combination for use of any preceding embodiment further comprising vitamin C.

31. The combination for use of any one of embodiments 24 to 30, wherein the combination comprises an oral dosage form comprising one or more of magnesium stearate, lactose, dextrose, microcrystalline cellulose, starch (corn), silica (silicon dioxide), titanium dioxide, zinc oxide, colostrum, hydroxypropyl methyl cellulose, stearic acid, sodium starch glycolate, gelatin, talc, sucrose, calcium stearate, and povidone, preferably, wherein the oral dosage form comprises magnesium stearate, microcrystalline cellulose, zinc oxide and colostrum.

32. The combination for use of any one of embodiments 24 to 31, wherein the combination comprises an oral dosage form comprising one or more flavourings, sweeteners and/or pigments.

33. The combination for use of any one of embodiments 24 to 32, wherein the treatment comprises administration of at least 0.24 mmol of the iodide salt, and at least 40 mg of the lactoperoxiase on a daily basis, preferably, the treatment comprises administration of at least 0.36 mmol of the iodide salt and at least 60 mg of the lactoperoxidase on a daily basis, more preferably, the treatment comprises administration of at least 0.48 mmol of the iodide salt and at least 80 mg of the lactoperoxidase on a daily basis.

34. The combination for use of any one of embodiments 24 to 33, wherein the treatment comprises administration of from 40 mg to 200 mg of the iodide salt, and from 40 mg to 200 mg of the lactoperoxidase to the equid on a daily basis, such as from 60 mg to 200 mg of the iodide salt and from 60 mg to 200 mg of the lactoperoxidase to the equid on a daily basis, optionally from 80 mg to 100 mg of the iodide salt and from 80 mg to 100 mg of the lactoperoxidase to the equid on a daily basis.

35. The combination for use of any one of embodiments 24 to 34, wherein the treatment comprises administration of at least 40 mg of the iodide salt, and at least 40 mg of the lactoperoxidase on a daily basis, preferably wherein the treatment comprises administration of at least 60 mg of the iodide salt and at least 50 mg of the lactoperoxidase on a daily basis, for example, wherein the treatment comprises administration of at least 60 mg of the iodide salt and at least 60 mg of the lactoperoxidase on a daily basis, more preferably, wherein the treatment comprises administration of at least 80 mg of the iodide salt and at least 80 mg of the lactoperoxidase on a daily basis.

36. The combination for use of any one of embodiments 24 to 35, wherein the treatment comprises administration of 40 mg to 200 mg of the iodide salt, and 40 mg to 200 mg of the lactoperoxidase to the equid on a daily basis, such as from 60 mg to 200 mg of the iodide salt and 60 mg to 200 mg of the lactoperoxidase to the equid on a daily basis, optionally from 80 mg to 100 mg of the iodide salt and 80 mg to 100 mg of the lactoperoxidase to the equid on a daily basis.

37. A feed additive composition or dietary supplement composition comprising:
lactoperoxidase, and
an iodide salt,
wherein the composition does not comprise a peroxide or a source of peroxide; and
wherein the composition does not comprise thiocyanate, or a source of thiocyanate;
wherein the lactoperoxidase is present in an amount of at least 40 mg, and wherein the iodide salt is present in an amount of at least 0.24 mmol,
optionally, wherein the weight ratio of the lactoperoxidase to the iodide salt is in the range of from 1:1.3 to 1.3:1;
optionally, wherein the iodide salt is selected from sodium iodide, potassium iodide, lithium iodide, ammonium iodide, calcium iodide, caesium iodide, hydrogen iodide, rhodium iodide and combinations thereof, preferably the iodide salt is sodium iodide and/or potassium iodide, more preferably the iodide salt is potassium iodide; and/or
optionally, wherein the composition is in tablet form, powder form, liquid form or oral suspension form.

38. The feed additive composition or dietary supplement composition according to embodiment 37, comprising at least 0.36 mmol of the iodide salt and at least 60 mg of the lactoperoxidase, preferably, at least 0.48 mmol of the iodide salt and at least 80 mg of the lactoperoxidase.

39. The feed additive composition or dietary supplement composition according to embodiment 37 or 38 comprising 0.24 mmol to 1.2 mmol of the iodide salt, preferably, 0.24 mmol to 0.6 mmol of the iodide salt, optionally, the feed additive comprises 0.36 mmol to 1.2 mmol of the iodide salt, such as 0.36 mmol to 0.6 mmol of the iodide salt, most preferably 0.24 mmol to 0.51 mmol of the iodide salt.

40. The feed additive composition or dietary supplement composition according to any one of embodiments 37 to 39, wherein the iodide salt is potassium iodide, and said composition comprises 40 to 200 mg of the potassium iodide, preferably, 40 to 120 mg of the potassium iodide, optionally 40 to 100 mg of the potassium iodide, most preferably 40 to 85 mg.

41. The feed additive composition or dietary supplement composition according to any one of embodiments 37 to 40, wherein said composition is formulated as a unit dosage form, wherein a unit dose comprises 5 to 20 mg lactoperoxidase, preferably, 8 to 15 mg lactoperoxidase, more preferably, 8 to 12 mg lactoperoxidase.

42. The feed additive composition or dietary supplement composition according to any one of embodiments 37 to 41, wherein said composition is formulated as a unit dosage form, wherein the lactoperoxidase present in an amount of from about 0.5 wt % to about 15 wt %, preferably from about 0.5 wt % to about 5 wt %, more preferably from about 1 wt % to about 2 wt %, such as from about 1 wt % to about 1.5 wt %, based on the total weight of the unit dose.

43. The feed additive composition or dietary supplement composition according to any one of embodiments 37 to 42, wherein said composition is formulated as a unit dosage form comprising 0.03 mmol to 0.12 mmol iodide salt, preferably, 0.048 mmol to 0.09 mmol iodide salt, more preferably, 0.048 mmol to 0.072 mmol iodide salt.

44. The feed additive composition or dietary supplement composition according to any one of embodiments 37 to 43, wherein said composition is formulated as a unit dosage form comprising iodide salt present in an amount of from about 0.5 wt % to about 15 wt %, preferably from about 0.5 wt % to about 5 wt %, more preferably from about 1 wt % to about 2 wt %, such as from about 1 wt % to about 1.5 wt % based on the total weight of the unit dose.

45. The feed additive composition or dietary supplement composition according to any one of embodiments 37 to 44, wherein the composition is formulated as a unit dosage form comprising 5 to 20 mg lactoperoxidase and 0.03 mmol to 0.12 mmol iodide salt, wherein the lactoperoxidase is present in an amount of from about 0.5 wt % to about 5 wt % based on the total weight of the unit dose and wherein the iodide salt is present in an amount of from about 0.5 wt % to about 5 wt % based on the total weight of the unit dose.

46. A method for treating and/or preventing equine gastric ulcer syndrome, comprising administering to an equid in need thereof a composition comprising lactoperoxidase, an iodide salt, and a pharmaceutically acceptable carrier and/or excipient, thereby treating or preventing equine gastric ulcer syndrome.

47. The method of embodiment 46, wherein the equine gastric ulcer syndrome comprises equine squamous gastric disease and/or equine glandular gastric disease.

48. The method of embodiment 46 or 47, wherein the lactoperoxidase and iodide salt are in a weight ratio of from 1:10 to 10:1, preferably, from 1:3 to 3:1, most preferably from 1:1.3 to 1.3:1, such as about 1:1.

49. The method of any one of embodiments 46 to 48, wherein the iodide salt is selected from sodium iodide, potassium iodide, lithium iodide, ammonium iodide, calcium iodide, caesium iodide, hydrogen iodide, rhodium iodide or combinations thereof.

50. The method of any one of embodiments 46 to 49, wherein the iodide salt is sodium iodide and/or potassium iodide, more preferably the iodide salt is potassium iodide.

51. The method of any one of embodiments 46 to 50, wherein the method comprises administration of from 0.24 mmol to 1.2 mmol of the iodide salt, and from 40 mg to 200 mg of the lactoperoxidase to the equid on a daily basis.

52. The method of any one of embodiments 46 to 51, wherein the method comprises administration of from 0.36 mmol to 1.2 mmol of the iodide salt and from 60 mg to 200 mg of the lactoperoxidase to the equid on a daily basis.

53. The method of any one of embodiments 46 to 52, wherein the method comprises administration of from 0.48 mmol to 0.60 mmol of the iodide salt and from 80 mg to 100 mg of the lactoperoxidase to the equid on a daily basis.

54. The method of any one of embodiments 46 to 53, wherein the method comprises administration of from 40 mg to 200 mg of the iodide salt, and from 40 mg to 200 mg of the lactoperoxidase to the equid on a daily basis.

55. The method of any one of embodiments 46 to 54, wherein the method comprises administration of from 60 mg to 200 mg of the iodide salt and from 60 mg to 200 mg of the lactoperoxidase to the equid on a daily basis.

56. The method of any one of embodiments 46 to 55, wherein the method comprises administration of from 80 mg to 100 mg of the iodide salt and from 80 mg to 100 mg of the lactoperoxidase to the equid on a daily basis.

57. The method of any one of embodiments 46 to 56, wherein the method comprises administration of one or more oral dosage forms.

58. The method of any one of embodiments 46 to 57, wherein method comprises administration of one or more unit doses of the composition.

59. The method of any one of embodiments 58, wherein a unit dose of the composition comprises from 5 mg to 50 mg lactoperoxidase, and wherein the unit dose of the composition comprises from 0.030 mmol to 0.30 mmol iodide salt.

60. The method of any one of embodiments 58 or 59, wherein a unit dose of the composition comprises from 8 mg to 20 mg lactoperoxidase, and wherein the unit dose of the composition comprises from 0.048 mmol to 0.12 mmol iodide salt.

61. The method of any one of embodiments 58 to 60, wherein a unit dose of the composition comprises lactoperoxidase present in an amount of from about 8 mg to about 20 mg, and in an amount of from about 0.5 wt % to about 5 wt % based on the total weight of the unit dose, and wherein the iodide salt is potassium iodide, and is present in an amount of from about 8 mg to about 20 mg, and in an amount of from about 0.5 wt % to about 5 wt % based on the total weight of the unit dose.

62. The method of any one of embodiments 46 to 61, wherein the composition comprises vitamin C and/or zinc oxide.

63. The method of any one of embodiments 46 to 62, wherein the equid is a horse or a pony.

64. A method for treating and/or preventing equine gastric ulcer syndrome, comprising administering to a horse in need thereof a combination comprising:
 a lactoperoxidase; and
 an iodide salt;
 wherein the lactoperoxidase and iodide salt are administered sequentially or simultaneously to the equid, thereby treating or preventing equine gastric ulcer syndrome.

65. The method of embodiment 64, wherein the lactoperoxidase and iodide salt are administered in a relative weight ratio of from about 1:2 to 2:1, more preferably in a relative weight ratio of from about 1:1.3 to 1.3:1.

66. The method of embodiment 64 or 65, comprising administering from 0.36 mmol to 1.2 mmol of the iodide salt and from 60 mg to 200 mg of the lactoperoxidase to the horse on a daily basis.

67. The method of any one of embodiments 64 to 44, wherein the equine gastric ulcer syndrome is equine squamous gastric disease or equine glandular gastric disease.

68. The method of any one of embodiments 64 to 67, wherein the equine gastric ulcer syndrome is equine glandular gastric disease.

69. A method for treating equine gastric ulcer syndrome, comprising administering to a horse in need thereof a composition comprising lactoperoxidase, an iodide salt, and a pharmaceutically acceptable carrier and/or excipient, wherein the iodide salt comprises potassium iodide, wherein the lactoperoxidase and potassium iodide are in a weight ratio of from 1:3 to 3:1,
 wherein the composition is formulated as a solid oral dosage form,
 wherein the composition does not comprise a peroxide or a source of peroxide,
 wherein the composition does not comprise thiocyanate or a source of thiocyanate,
 wherein the method comprises administration of from 0.36 mmol to 0.6 mmol of the iodide salt and from 60 mg to 100 mg of the lactoperoxidase to the horse on a daily basis, thereby treating equine gastric ulcer syndrome.

70. The method of embodiment 69, comprising administering one or more unit doses of the solid oral dosage form, wherein a unit dose of the solid dosage form comprises: lactoperoxidase present in an amount of from about 8 mg to about 20 mg, and in an amount of from about 0.5 wt % to about 5 wt % based on the total weight of the unit dose, and wherein the iodide salt is potassium iodide, and is present in an amount of from about 8 mg to about 20 mg, and in an amount of from about 0.5 wt % to about 5 wt % based on the total weight of the unit dose.

71. The method of embodiment 69 or 70, wherein said composition comprises vitamin C and zinc oxide.

72. The method of any one of embodiments 69 to 71, wherein the lactoperoxidase and potassium iodide are in a weight ratio of from 1:1.3 to 1.3:1.

73. The method of any one of embodiments 69 to 72, wherein the method comprises administering from 0.48 mmol to 0.6 mmol of the iodide salt and from 80 mg to 100 mg of the lactoperoxidase to the horse on a daily basis.

74. The method of any one of embodiments 69 to 73, wherein the equine gastric ulcer syndrome is equine squamous gastric disease or equine glandular gastric disease.

75. The method of any one of embodiments 69 to 74, wherein the equine gastric ulcer syndrome is equine glandular gastric disease.

The invention claimed is:

1. A method for treating equine gastric ulcer syndrome, comprising administering to an equid in need thereof a therapeutically effective amount of a composition comprising lactoperoxidase, an iodide salt, and a pharmaceutically acceptable carrier and/or excipient, thereby treating the equine gastric ulcer syndrome.

2. The method of claim 1, wherein the equine gastric ulcer syndrome comprises equine squamous gastric disease and/or equine glandular gastric disease.

3. The method of claim 1, wherein the lactoperoxidase and iodide salt are in a weight ratio of from 1:3 to 3:1.

4. The method of claim 1, wherein the iodide salt is selected from the group consisting of sodium iodide, potassium iodide, lithium iodide, ammonium iodide, calcium iodide, cesium iodide, hydrogen iodide, rhodium iodide or combinations thereof.

5. The method of claim 1, wherein the iodide salt is sodium iodide and/or potassium iodide.

6. The method of claim 1, wherein the method comprises administration of from 0.24 mmol to 1.2 mmol of the iodide salt, and from 40 mg to 200 mg of the lactoperoxidase to the equid on a daily basis.

7. The method of claim 1, wherein the method comprises administration of from 0.36 mmol to 1.2 mmol of the iodide salt and from 60 mg to 200 mg of the lactoperoxidase to the equid on a daily basis.

8. The method of claim 1, wherein the method comprises administration of from 0.48 mmol to 0.60 mmol of the iodide salt and from 80 mg to 100 mg of the lactoperoxidase to the equid on a daily basis.

9. The method of claim 1, wherein the method comprises administration of from 40 mg to 200 mg of the iodide salt, and from 40 mg to 200 mg of the lactoperoxidase to the equid on a daily basis.

10. The method of claim 1, wherein the method comprises administration of from 60 mg to 200 mg of the iodide salt and from 60 mg to 200 mg of the lactoperoxidase to the equid on a daily basis.

11. The method of claim 1, wherein the method comprises administration of from 80 mg to 100 mg of the iodide salt and from 80 mg to 100 mg of the lactoperoxidase to the equid on a daily basis.

12. The method of claim 1, wherein the method comprises administration of one or more oral dosage forms.

13. The method of claim 1, wherein method comprises administration of one or more unit doses of the composition.

14. The method of claim 1, wherein the composition comprises vitamin C and/or zinc oxide.

15. The method of claim 1, wherein the equid is a horse or a pony.

16. A method for treating equine gastric ulcer syndrome, comprising administering to a horse in need thereof two separate compositions comprising therapeutically effective amounts of
a lactoperoxidase in one composition; and an iodide salt in the other composition; wherein the lactoperoxidase and iodide salt are administered sequentially or simultaneously to the horse, and wherein the composition comprising the iodide salt is administered orally, thereby treating the equine gastric ulcer syndrome.

17. The method of claim 16, wherein the lactoperoxidase and iodide salt are administered in a relative weight ratio of from about 1:2 to 2:1.

18. The method of claim 16, comprising administering 0.36 mmol to 1.2 mmol of the iodide salt and 60 mg to 200 mg of the lactoperoxidase to the horse on a daily basis.

19. The method of claim 16, wherein the equine gastric ulcer syndrome is equine squamous gastric disease or equine glandular gastric disease.

20. The method of claim 16, wherein the equine gastric ulcer syndrome is equine glandular gastric disease.

21. A method for treating equine gastric ulcer syndrome, comprising administering to a horse in need thereof a therapeutically effective amount of a composition comprising lactoperoxidase, an iodide salt, and a pharmaceutically acceptable carrier and/or excipient, wherein the iodide salt comprises potassium iodide, wherein the lactoperoxidase and potassium iodide are in a weight ratio of from 1:3 to 3:1, wherein the composition is formulated as a solid oral dosage form, wherein the composition does not comprise a peroxide or a source of peroxide, wherein the composition does not comprise thiocyanate or a source of thiocyanate, wherein the method comprises administration of from 0.36 mmol to 0.6 mmol of the iodide salt and from 60 mg to 100 mg of the lactoperoxidase to the horse on a daily basis, thereby treating the equine gastric ulcer syndrome.

22. The method of claim 21, wherein said composition comprises vitamin C and zinc oxide.

23. The method of claim 21, wherein the lactoperoxidase and potassium iodide are in a weight ratio of from 1:1.3 to 1.3:1.

24. The method of claim 21, wherein the method comprises administering from 0.48 mmol to 0.6 mmol of the iodide salt and from 80 mg to 100 mg of the lactoperoxidase to the horse on a daily basis.

25. The method of claim 21, wherein the equine gastric ulcer syndrome is equine squamous gastric disease or equine glandular gastric disease.

26. The method of claim 21, wherein the equine gastric ulcer syndrome is equine glandular gastric disease.

\* \* \* \* \*

UNITED STATES PATENT AND TRADEMARK OFFICE
CERTIFICATE OF CORRECTION

| | | |
|---|---|---|
| PATENT NO. | : 12,311,014 B1 | Page 1 of 1 |
| APPLICATION NO. | : 18/889340 | |
| DATED | : May 27, 2025 | |
| INVENTOR(S) | : Killian O'Briain | |

It is certified that error appears in the above-identified patent and that said Letters Patent is hereby corrected as shown below:

On the Title Page

Add item (30) Foreign Application Priority Data:
November 24, 2023 (EP) .................. 23211903

In the Claims

Claim 3, Column 46, Lines 34:
Delete "from"

Signed and Sealed this
Second Day of September, 2025

Coke Morgan Stewart
*Acting Director of the United States Patent and Trademark Office*